(12) United States Patent
Feng

(10) Patent No.: US 8,946,159 B2
(45) Date of Patent: Feb. 3, 2015

(54) ADMINISTRATION OF AN ANTAGONIST OF α5β1 FOR ANTI-ANGIOGENESIS AND CANCER TREATMENT

(75) Inventor: Xiaodong Feng, Carmichael, CA (US)

(73) Assignee: California Northstate College of Pharmacy, LLC, Elk Grove, CA (US)

( * ) Notice: Subject to any disclaimer, the term of this patent is extended or adjusted under 35 U.S.C. 154(b) by 0 days.

(21) Appl. No.: 13/374,369

(22) Filed: Dec. 22, 2011

(65) Prior Publication Data

US 2013/0165380 A1    Jun. 27, 2013

(51) Int. Cl.
```
A61K 38/00      (2006.01)
A61P 35/00      (2006.01)
C07K 14/515     (2006.01)
A61K 38/17      (2006.01)
A61K 38/18      (2006.01)
A61K 45/06      (2006.01)
```

(52) U.S. Cl.
CPC ......... *A61K 38/1767* (2013.01); *A61K 38/1891* (2013.01); *A61K 45/06* (2013.01)
USPC .......................... 514/13.3; 514/1.1; 514/19.3

(58) Field of Classification Search
None
See application file for complete search history.

(56) References Cited

U.S. PATENT DOCUMENTS

| | | | |
|---|---|---|---|
| 6,852,318 B1 * | 2/2005 | Varner | 424/130.1 |
| 7,074,408 B2 * | 7/2006 | Fanslow et al. | 424/185.1 |
| 7,910,609 B2 * | 3/2011 | DeGrado et al. | 514/327 |
| 8,008,256 B2 * | 8/2011 | Markland et al. | 514/19.3 |
| 2004/0121031 A1 | 6/2004 | Majeed et al. | |
| 2005/0260210 A1 | 11/2005 | Ramakrishnan et al. | |
| 2008/0267978 A1 | 10/2008 | Zutter | |
| 2010/0105644 A1 | 4/2010 | Varani et al. | |
| 2010/0291034 A1 | 11/2010 | Ralston, II et al. | |
| 2011/0165075 A1 | 7/2011 | Rajopadhye et al. | |
| 2011/0319335 A1 * | 12/2011 | Feng | 514/19.3 |
| 2012/0052095 A1 | 3/2012 | Chaniyilparampu et al. | |
| 2012/0177757 A1 | 7/2012 | Hidmi et al. | |

FOREIGN PATENT DOCUMENTS

WO    PCT US2012/70399    12/2012

OTHER PUBLICATIONS

Knight L et al "Differences in binding of 99mTc-disintegrins to integrin avb3 on tumor and vascular cells" Nuclear Medicine and Biology 34:371-381. Published Nov. 2007.*
Staniszewsak I et al "Effect of VP12 and viperistatin on inhibition of collagen receptors-dependent melanoma metastasis" Cancer Biol and Thera 8:1507-1516. Published Aug. 1, 2009.*
U.S. Appl. No. 12/821,873, filed Jun. 23, 2012, Feng.
U.S. Appl. No. 13/671,423, filed Nov. 7, 2012, Feng.
U.S. Appl. No. 13/671,462, filed Nov. 7, 2012, Feng.
Laurens, et al., Fibrin Structure and Wound Healing, J Thromb Haemost, May 2006, 4(5), pp. 932-939.
Lugade, Local Radiation Therapy of B16 Melanoma Tumors Increases the Generation of Tumor Antigen-Specific Effector Cells That Traffic to the Tumor J Immunol 2005;174:7516-7523.
Marcinkiewicz, Immunological characterization of eristostatin and echistatin binding sites on allb b3 and avb3 integrinsBiochem J.(1996)317,817-825.
Pimton, P., et al. "Fibronectin-mediated upregulation of α5β1 intergrin and cell adhesion during differentiation of mouse embryonic stem cells" Cell Adhesion & Migration, vol. 5, No. 1, pp. 73-82 (Jan.-Feb. 2011) see p. 74, right col. p. 76, right col. p. 79, left column.
Sabherwal, et al. Intergri Alpha 2 Beta 1 mediates the anti-angiogenic and anti-tumor activities of angiocidin, a novel tumor-associated protein, Experimental Cell Research, Aug. 2006, 312(13), pp. 2443-2453.
Smith P.K. et al. Measurement of protein using bicinchoninic acid , Anal Biochem 1985, 150(1);76-85.
Sitterley, Disintegrins BioFiles 2008, 3.8.6.
Sottile, Regulation of Angiogenesis by Extracellular Matrix, Biochim Biophsy Acta, Mar. 2004, 1654(1) pp. 13-22.
Tonnesen, et al Angiogenesis in Wound Healing, J Investig Dermatol Symp Proc, Dec. 2000, 5(1), pp. 40-46.
Xu, J., et al., Extracellular Matrix Alters PDGF Regulation of Fibroblast Integrins, J Cell Biol, Jan. 1996, 132(1-2), pp. 239-249.
Beviglia, et al. Effect of four disintegrins on the adhesive and metastatic properties of B1B6F10 melanoma cells in a murine model. Oncol Res.1995:7(1): abstract only.
Calvete, J.J., et al., Snake Venom Disintegrins: Novel Dimeric Disintegrins and Structural Diversification by Disulphide Bond Engineering, Biochem J., Jun. 2003, 372, pp. 725-734.
European Association of Cancer Research annual meeting in Olso, Norway Jun. 26-29 (Poster).
Ferrara, et al., Angiogenesis as a Therapeutic Target, Nature, Dec. 15, 2005, 438(7070), pp. 967-975.
Feng et al. Fibrin and collagen differently, but synergistically regulate sprout angiogenesis of human dermal microvascular endothelial cells in 3-dimensional matrix. International Journal of Cell Biology vol. 2013, Article ID 231279, 11 pages.
Kirsch, Cancer Treat Res 117:Abstract only (2004).
International Search Report for PCT US2012/70399, Feng.
Zetter, Annu. Rev. Med. 49:407-24(1998).

* cited by examiner

*Primary Examiner* — Maury Audet
*Assistant Examiner* — Zachary J Miknis
(74) *Attorney, Agent, or Firm* — Brian S. Boyer; Syndicated Law, PC

(57) ABSTRACT

A combination therapy is provided and is directed to pharmaceutical compositions and methods for administering a combination of an α5β1 antagonist with an α2β1 antagonist to a subject. The methods are for use in inhibiting, preventing, or reversing angiogenesis, as well as in treating cancer. The compositions and methods include a combined administration of VLO4 and VP12 (ECL12).

29 Claims, 13 Drawing Sheets ately, one of skill will appreciate a composition and method of treatment that can not only inhibit angiogenesis, but that can also disrupt the physical and mechanical architecture within which angiogenesis takes place. Such a composition and method may be able to, at least, (i) inhibit or prevent angiogenesis; (ii) treat solid tumors to contain and/or reduce tumor size; and (iii) inhibit or prevent the tumor invasion that leads to metastasis within a subject.

ADMINISTRATION OF AN ANTAGONIST OF α5β1 FOR ANTI-ANGIOGENESIS AND CANCER TREATMENT

SEQUENCE LISTING

The instant application contains a Sequence Listing which has been submitted in ASCII format via EFS-Web and is hereby incorporated by reference in its entirety. Said ASCII copy, created on Jun. 25, 2012, is named CALPP2US.txt and is 4,387 bytes in size.

BACKGROUND

1. Field of the Invention

The teachings provided herein relate to pharmaceutical compositions comprising an α5β1 antagonist for use in inhibiting angiogenesis and treating cancer, which can also be used in combination with an α2β1 antagonist and in a pharmaceutically acceptable carrier.

2. Description of Related Art

Solid tumor growth is generally considered to be angiogenesis-dependent, such that the control of neovascularization in cancerous tissue is one of the goals of cancer research. As such, various potential angiogenesis inhibitors have been investigated in the treatment of solid tumors and metastasis using anti-angiogenic therapy. Unfortunately, however, a particularly effective method of using an agent or combination of agents remain to be discovered that, at least, (i) inhibits or prevents angiogenesis; (ii) treats solid tumors to contain and/ or reduce tumor size; and (iii) inhibits or prevents the tumor invasion that leads to metastasis within a subject.

The art is still in need of improved angiogenesis inhibitors, as well cancer therapies that include such inhibitors. Angiogenesis is a highly regulated event that involves complex, dynamic interactions between microvascular endothelial cells and extracellular matrix (ECM) proteins. Control of angiogenesis can be used in a variety of treatments, including cancer therapy. Alteration of ECM composition and architecture is a hallmark of wound clot and tumor stroma. The role of ECM in regulation of angiogenesis associated with wound healing and tumor growth still remain generally undefined in the art. During angiogenesis, however, endothelial cell responses to growth factors are modulated by the compositional and mechanical properties of a surrounding three-dimensional (3D) extracellular matrix (ECM) that is dominated by either cross-linked fibrin or type I collagen.

Likewise, a novel method to control tumor invasion to treat a metastatic disease, for example, would be seen as a significant contribution to the art by one of skill. Over 60% of breast cancer patients have metastatic disease at diagnosis. The most common cause of death in breast cancer patients is due to the metastatic spread of the cancer cells from the primary tumor site to remote sites and growth of the breast cancer cells at the distant location. Metastasis is a complex process including several mechanisms: (1) migration of the tumor cells through the extracellular matrix surrounding the tumor; (2) invasion of tumor cells into angiogenic blood vessels growing into the tumor; (3) adhesion of the metastatic cell at a distant site where the microenvironment is receptive to tumor growth; and (4) newly attached cells must proliferate and induce angiogenesis at the metastatic site. As such, a combination of select inhibitors could possibly limit this process.

Accordingly, and for at least the above reasons, one of skill will appreciate a method of inhibiting, preventing, or even reversing, angiogenesis. Moreover, one of skill will appreciate a composition and method of treatment that can not only

SUMMARY

The teachings provided herein generally relate to pharmaceutical compositions and methods comprising an α5β1 antagonist for use in inhibiting, preventing, or reversing angiogenesis and treating cancer when used in combination with an α2β1 antagonist and in a pharmaceutically acceptable carrier. In some embodiments, the teachings are directed to a pharmaceutical formulation comprising an α5β1 antagonist, an α2β1 antagonist, and a pharmaceutically acceptable carrier. The pharmaceutical formulation can, for example, comprise VLO4 and VP12 (ECL12). In some embodiments, the teachings are directed to an article of manufacture comprising an α5β1 antagonist, an α2β1 antagonist, and instructions for administering an effective amount of the α5β1 antagonist and an effective amount of the α2β1 antagonist to a subject.

In some embodiments, the methods are directed to inhibiting angiogenesis in a subject, comprising administering an effective amount of an α5β1 antagonist in combination with an effective amount of an α2β1 antagonist to the subject. The methods can comprise, for example, administering and effective amount of VLO4 and VP12 (ECL12) to the subject. In some embodiments, the method further inhibits tumor invasion. And, in some embodiments, the method can inhibit the growth of solid tumors.

In some embodiments, the methods taught herein can further include the administration of an effective amount of an antiproliferative. And, in some embodiments, the methods can include the administration of an effective amount of radiation therapy.

In some embodiments, the methods can be directed to inhibiting angiogenesis, inhibiting tumor invasion, inhibiting the growth of solid tumors, or a combination thereof, in a subject. In these embodiments, as described above, the methods can further comprise the administration of an effective amount of an antiproliferative, an effective amount of radiation therapy, surgical therapy, or a combination thereof.

VLO4 can be effective when administered alone, or in combination with VP12 (ECL12). The teachings include, for example, a method of reversing angiogenesis in a subject, comprising administering an effective amount of an VLO4 to the subject. In some embodiments the methods include administering VLO4 and VP12 (ECL12) to the subject. In some embodiments, the method further inhibits tumor invasion, inhibits angiogenesis, and/or inhibits the growth of solid tumors. Moreover, in some embodiments, the methods can further comprise the administration of an effective amount of an antiproliferative and/or radiation therapy. As such, in some embodiments, the methods further comprise the administration of an effective amount of chemotherapy.

One of skill reading the teachings that follow will appreciate that the concepts can extend into additional embodiments that go well-beyond a literal reading of the claims, the inventions recited by the claims, and the terms recited in the claims.

DETAILED DESCRIPTION

Figure 1:
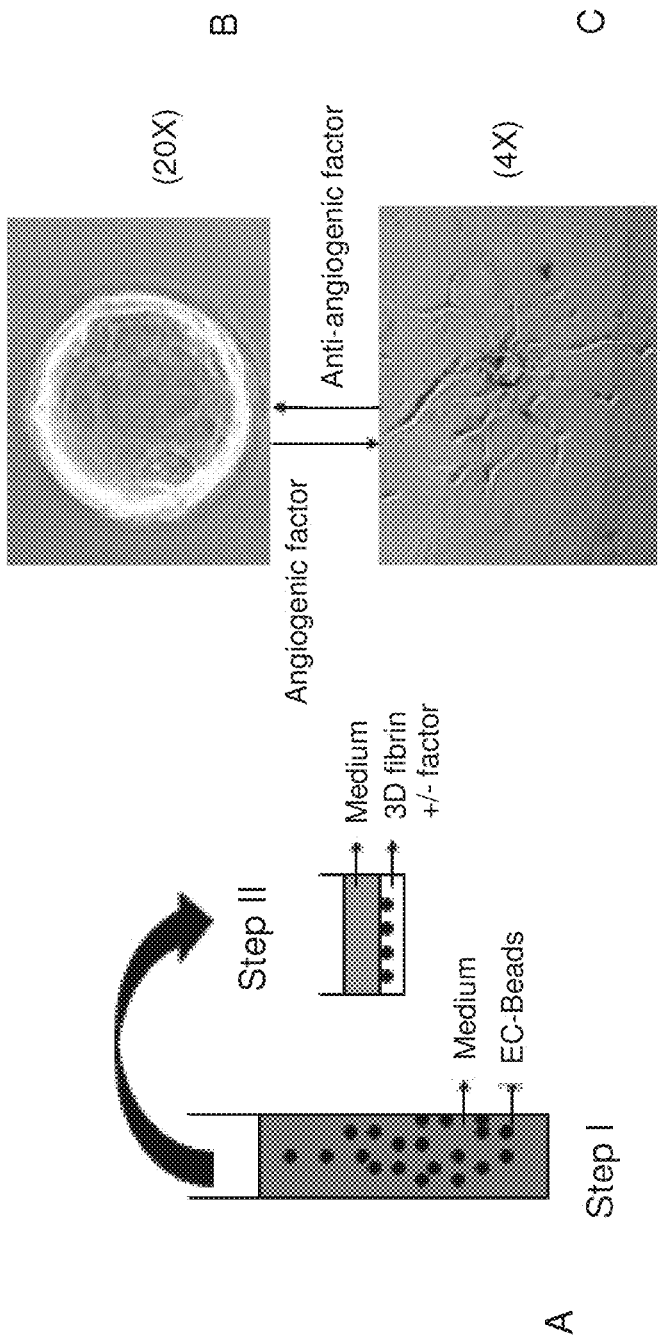
FIGS. 1A-1C illustrate a study of human microvascular endothelial cell angiogenesis, according to some embodiments.

The teachings provided herein generally relate to pharmaceutical compositions and methods comprising an $\alpha5\beta1$ antagonist for use in inhibiting, preventing, or reversing angiogenesis and treating cancer when used in combination with an $\alpha2\beta1$ antagonist and in a pharmaceutically acceptable carrier.

In some embodiments, the teachings are directed to a pharmaceutical formulation comprising an $\alpha5\beta1$ antagonist, an $\alpha2\beta1$ antagonist, and a pharmaceutically acceptable carrier. In some embodiments, the teachings are directed to an article of manufacture comprising an $\alpha5\beta1$ antagonist, an $\alpha2\beta1$ antagonist, and instructions for administering an effective amount of the $\alpha5\beta1$ antagonist and an effective amount of the $\alpha2\beta1$ antagonist to a subject. In some embodiments, the terms "composition" and "formulation" can be interchangeable.

In some embodiments, the teachings are directed methods of inhibiting angiogenesis in a subject, comprising administering an effective amount of an $\alpha5\beta1$ antagonist in combination with an effective amount of an $\alpha2\beta1$ antagonist to the subject. In some embodiments, the method further inhibits tumor invasion. And, in some embodiments, the method can inhibit the growth of solid tumors.

The $\alpha5\beta1$ antagonist can include, for example, any chemical moiety that functions to block $\alpha5\beta1$. Likewise, the $\alpha2\beta1$ antagonist can include, for example, any chemical moiety that functions to block $\alpha2\beta1$. Such antagonists can include small molecules, such as small molecule pharmaceuticals, or large molecules, such as peptides, oligopeptides, polypeptides, proteins, nucleic acids, oligonucleotides, and polynucleotides, for example. In some embodiments, the peptide can include an RGD-recognition motif. In some embodiments, an antagonist can include an antibody such as, for example, a polyclonal antibody or a monoclonal antibody and, in some embodiments, the antibody can be humanized or fully human. The antibody may already be known to bind to an $\alpha5\beta1$ antagonist, an $\alpha2\beta1$ antagonist, or a combination thereof; or, the antibody can be designed specifically to bind to an $\alpha5\beta1$ antagonist, an $\alpha2\beta1$ antagonist, or a combination thereof. One of skill will how to select and/or design an antibody of interest for use with the methods provided herein and can appreciate, for example, that there are known methods of producing a desired antibody. As such, any inhibitor, or ligand, that binds to, and down-regulates, the activity of angiogenesis and/or collagen matrix formation can be used in some embodiments. Such inhibitors can include, but are not limited to, disintegrins, RGD peptides, blocking monoclonal antibodies, chemical inhibitors, antisense mRNA, and the like, or any combination thereof.

In some embodiments, the antagonists can include one or more of the disintegrins that bind to an $\alpha5\beta1$ antagonist, an $\alpha2\beta1$ antagonist, or a combination thereof. Examples of disintegrins can include disintegrins obtained from snake venom extracts. Such integrins can include, for example, RGD and non-RGD, such as KGD, MLD, VGD, and MVD disintegrins, referring to an active peptide sequence which can be, for example, in the "inhibitory loop" of the sequence.

For example, VLO4 can be effective when administered alone, or in combination with VP12 (ECL12). The teachings include, for example, a method of reversing angiogenesis in a subject, comprising administering an effective amount of an VLO4 to the subject. In some embodiments the methods include administering VLO4 and VP12 (ECL12) to the subject. In some embodiments, the method further inhibits tumor invasion, inhibits angiogenesis, and/or inhibits the growth of solid tumors. Moreover, in some embodiments, the methods can further comprise the administration of an effective amount of an antiproliferative and/or radiation therapy. As such, in some embodiments, the methods further comprise the administration of an effective amount of chemotherapy.

The disintegrins from snake venom can comprise (i) a first group of single chain sequence compounds having about 49-51 residues and four disulphide bonds; (ii) a second group of single chain sequence compounds having about 70 residues and six disulphide bonds; (iii) a third group of single chain sequence compounds having about 84 residues cross-linked by seven disulphide bonds; (iv) a fourth group of single chain sequence compounds having about 100 residues having 16 Cys residues involved in forming eight disulphide bonds; and (v) a fifth group of dimeric compounds having homodimers or heterodimers. The dimeric disintegrins can contain, for example, about 67 residues in each subunit, with ten cysteine residues involved in forming four intrachain disulphide bonds and two interchain cysteine linkages.

In some embodiments, the disintegrins can include echistatin, VLO4, VP12 (ECL12), or a combination thereof. In some embodiments the disintegrins can comprise (i) echistatin, eristocophin, eristostatin, and ocellatusin; (ii) trigramin, kistrin, flavoridin, albolabrin, and barbourin; (iii) bitistatin and salmosin 3; (iv) PIII; and (v) contortrostatin, EC3, bilitoxin, and EMF-10; and a combination thereof. And, in some embodiments, the disintegrins can include, for example, EO4, EO5, EMS11, VLO4, VLO5, VB7, VA6, or a combination thereof. U.S. application Ser. No. 12/821,873 is hereby incorporated herein by reference in it's entirety.

In some embodiments, the methods can comprise, for example, administering and effective amount of echistatin and VP12 (ECL12) to the subject. In some embodiments, contortrostatin may be used in place of, or in addition to, VP12 (ECL12). In some embodiments, an RGD peptide that blocks α5β1 integrin activity can be used in combination with a monoclonal antibody that blocks α2β1 integrin activity.

The antagonists include proteins, such as the disintegrins. And, any polypeptide having at least 80%, 85%, 90%, 91%, 92%, 93%, 94%, 95%, 96%, 97%, 98%, 99% identity to one of the proteins taught herein can be used. The term "identity" can be used to refer to the extent to which sequences are invariant. The identity can be referenced against an entire protein or a defined fragment of the protein, as well as, perhaps combination of protein fragments in the case of a construct of peptide fragments. Computational approaches to sequence alignment are general either global or local alignments. Calculating a global alignment is a form of global optimization that "forces" the alignment to span the entire length of all query sequences. By contrast, local alignments can be used to identify regions of similarity within long sequences that are often widely divergent overall. Local alignments can be used, but can be more difficult to calculate because of the additional challenge of identifying the regions of similarity. One of skill will appreciate that a variety of computational algorithms are available, including slow but formally optimizing methods like dynamic programming, and efficient, but not as thorough heuristic algorithms or probabilistic methods designed for large-scale database search. In some embodiments, the sequence alignments for identity can be local, global, dynamic, progressive, heuristic or probabilistic. And, in some embodiments, the sequence alignments can even be based around the location of a motif of interest, such as an active region of the protein sought for binding. The motif in the disintegrins, for example, can include the inhibitory loop region, an RGD region, a comparable non-RGD active region, or a combination thereof. One of skill can readily compare sequence identity for any of a number of desired purposes such as, for example, assessing the possibility of binding to a receptor, functioning as an agonist, antagonist, and the like, given the knowledge of the function of a like protein or peptide structure. Examples of programs that can be used to determine identity or homology include, for example, BLAST and FASTA.

A polypeptide can include a variant or mutant of the protein, a chimeric construct, a fragment, a construct of at least two linked peptide fragments, variants of the fragments, a dimer, and the like. Any of the polypeptides taught herein can be produced using recombinant procedures known to one of skill, or using synthetic procedures in which the amino acid sequence can be constructed, for example, using liquid or solid phase synthesis techniques, such as Fmoc or Boc methods. Likewise, any of the polypeptides taught herein can be isolated and/or purified using procedures known to one of skill, such as through the use of affinity tags, and the like. In some embodiments, the polypeptides can include the inhibitory loop regions, RGD or non-RGD peptide fragments, linkers that include an amino acid, an amino acid sequence, alkylenes, or a combination thereof.

The term "variant" refers to modifications to a peptide that allows the peptide to retain its binding properties, and such modifications include, but are not limited to, conservative substitutions in which one or more amino acids are substituted for other amino acids; deletion or addition of amino acids that have minimal influence on the binding properties or secondary structure; conjugation of a linker; post-translational modifications such as, for example, the addition of functional groups. Examples of such post-translational modifications can include, but are not limited to, the addition of modifying groups described below through processes such as, for example, glycosylation, acetylation, phosphorylation, modifications with fatty acids, formation of disulfide bonds between peptides, biotinylation, PEGylation, and combinations thereof.

In many embodiments, the molecular weight of an agent should be at or below about 40,000 Daltons to ensure elimination of the agent from a subject. In some embodiments, the molecular weight of the agent ranges from about 300 Daltons to about 40,000 Daltons, from about 8,000 Daltons to about 30,000 Daltons, from about 10,000 Daltons to about 20,000 Daltons, or any range therein.

The variants can be merely conservatively modified variants of the polypeptides containing only conservative substitutions. The term "conservatively modified variant" refers to a conservative amino acid substitution, which is an amino acid substituted by an amino acid of similar charge density, hydrophilicity/hydrophobicity, size, and/or configuration such as, for example, substituting valine for isoleucine. In comparison, a "non-conservatively modified variant" refers to a non-conservative amino acid substitution, which is an amino acid substituted by an amino acid of differing charge density, hydrophilicity/hydrophobicity, size, and/or configuration such as, for example, substituting valine for phenylalanine.

In some embodiments, the methods taught herein can further include the administration of an effective amount of an additional bioactive agent or therapeutic treatment, such as the administration of an effective amount of an antiproliferative and/or an effective amount of radiation therapy. In some embodiments, the terms "agent" and "therapy" can be interchangeable. For example, the administration of radiation can be considered the administration of a second agent, in some embodiments.

A bioactive agent can be any moiety capable of contributing to a therapeutic effect, a prophylactic effect, both a therapeutic and prophylactic effect, or other biologically active effect in a subject. A bioactive agent can also have diagnostic properties. The bioactive agents include, but are not limited to, small molecules, nucleotides, oligonucleotides, polynucleotides, amino acids, oligopeptides, polypeptides, and proteins. Bioactive agents can include, but are not limited to, antiproliferatives, antineoplastics, antimitotics, anti-inflammatories, antiplatelets, anticoagulants, antifibrins, antithrombins, antibiotics, antiallergics, antioxidants, and any prodrugs, codrugs, metabolites, analogs, homologues, congeners, derivatives, salts and combinations thereof. It is to be appreciated that one skilled in the art should recognize that some of the groups, subgroups, and individual bioactive agents may not be used in some embodiments of the present invention.

Antiproliferatives include, for example, actinomycin D, actinomycin IV, actinomycin I1, actinomycin X1, actinomycin C1, and dactinomycin (Cosmegen®, Merck & Co., Inc.). Antineoplastics or antimitotics include, for example, paclitaxel (TAXOL, Bristol-Myers Squibb Co.), docetaxel (TAXOTERE, Aventis S.A.), methotrexate, azathioprine, vincristine, vinblastine, fluorouracil, doxorubicin hydrochloride (ADRIAMYCIN, Pfizer, Inc.) and mitomycin (MUTAMYCIN, Bristol-Myers Squibb Co.), and any prodrugs, codrugs, metabolites, analogs, homologues, congeners, derivatives, salts and combinations thereof. Antiplatelets, anticoagulants, antifibrin, and antithrombins include, for example, sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors (ANGIOMAX, Biogen, Inc.), and any prodrugs, codrugs, metabolites, analogs, homologues, congeners, derivatives, salts and combinations thereof. Cytostatic or antiproliferative agents include, for example, angiopeptin, angiotensin converting enzyme inhibitors such as captopril (CAPOTEN and CAPOZIDE, Bristol-Myers Squibb Co.), cilazapril or lisinopril (PRINVIL and PRINZIDE, Merck & Co., Inc.); calcium channel blockers such as nifedipine; colchicines; fibroblast growth factor (FGF) antagonists, fish oil (omega 3-fatty acid); histamine antagonists; lovastatin (MEVACOR, Merck & Co., Inc.); monoclonal antibodies including, but not limited to, antibodies specific for Platelet-Derived Growth Factor (PDGF) receptors; nitroprusside; phosphodiesterase inhibitors; prostaglandin inhibitors; suramin; serotonin blockers; steroids; thioprotease inhibitors; PDGF antagonists including, but not limited to, triazolopyrimidine; and nitric oxide, and any prodrugs, codrugs, metabolites, analogs, homologues, congeners, derivatives, salts and combinations thereof. Antiallergic agents include, but are not limited to, pemirolast potassium (ALAMAST, Santen, Inc.), and any prodrugs, codrugs, metabolites, analogs, homologues, congeners, derivatives, salts and combinations thereof.

Antibody therapy provides additional bioactive agents that may be useful when administered in combination with the methods taught herein. AVASTATIN, for example, is a human monoclonal antibody to VEGF, has provided beneficial results in colorectal cancer, increasing survival time by more than 30% when used in combination with the standard Saltz regime of irinotecan, 5-fluorouracil, and leucovorin. One of skill will appreciate that several monoclonal antibodies would be useful, the following providing further examples:

TABLE

| mAb name | Trade name | Cancer treated: |
|---|---|---|
| rituximab | RITUXAN | non-Hodgkin lymphoma |
| trastuzumab | HERCEPTIN | breast cancer |
| gemtuzumab ozogamicin* | MYLOTARG | acute myelogenous leukemia (AML) |
| alemtuzumab | CAMPATH | chronic lymphocytic leukemia (CLL) |
| ibritumomab tiuxetan* | ZEVALIN | non-Hodgkin lymphoma |
| tositumomab* | BEXXAR | non-Hodgkin lymphoma |
| cetuximab | ERBITUX | colorectal cancer; head & neck cancers |
| bevacizumab | AVASTIN | colorectal cancer; non-small cell lung cancer; breast cancer; glioblastoma; kidney cancer |
| panitumumab | VECTIBIX | colorectal cancer |
| ofatumumab | ARZERRA | chronic lymphocytic leukemia (CLL) |

*refers to a conjugated monoclonal antibody

It should be appreciated that, a bioactive agent can be given alone or in combination with other bioactive agents, with the compositions and methods taught herein. Chemotherapy drugs, for example, are sometimes most effective when given in combination, as a combination chemotherapy regime. The rationale for combination chemotherapy is to use drugs that work by different mechanisms of action, thereby decreasing the likelihood that resistant cancer cells will develop. When drugs having different effects are combined, each drug can be used at its optimal dose, sometimes without, and sometimes reducing, intolerable side effects.

For some cancers, the best approach may be a combination of surgery, radiation therapy, and/or chemotherapy. Surgery or radiation therapy, for example, treats cancer that is confined locally, while chemotherapy can be used to also kill the cancer cells that have spread to distant sites. Sometimes radiation therapy or chemotherapy can be given before surgery to shrink a tumor, thereby improving the opportunity for complete surgical removal, making these types of combination therapies a potentially valuable therapy for use with the teachings provided herein, at least in some embodiments. Radiation therapy and low-dose chemotherapy after surgery, for example, can help destroy remaining cancer cells. One of skill will appreciate that the stage of the cancer can be a considerable factor in determining whether single therapy or a combination is desired. For example, early-stage breast cancer may be treated with surgery alone, or by using surgery combined with radiation therapy, chemotherapy, or a combination thereof, depending on the size of the tumor and the risk of recurrence. Locally advanced breast cancer, for example, can be treated with chemotherapy, radiation therapy, and surgery, in some embodiments.

Any cancer tissue that relies, at least in part, on blood supply to survive, may be treatable in some embodiments. Examples of cancers that may be treated using the methods taught herein can include, but are not limited to, prostate, bladder, lung, breast, osteosarcoma, pancreatic, colon, melanoma, testicular, colorectal, urothelial, renal cell, hepatocellular, leukemia, lymphoma, and ovarian cancer and central nervous system malignancies. Lung cancer, although often disperse, may also be treated in some embodiments. Likewise, even liquid cancers, such as lymphoma and leukemia, including acute myeloid leukemia, may also be treated in some embodiments using methods that incorporate the teachings provided herein.

Sometimes the combinations taught herein may not be directed to a cure but, rather, to reduce symptoms and prolong life. Such combination therapies can be useful, for example, for subjects having advanced cancers that are not suitable for radiation therapy or surgical treatment, such as those having un-resectable non-small cell lung cancer, esophageal cancer, or bladder cancers, for example.

In some embodiments, the methods can comprise, for example, administering an effective amount of VLO4 and an effective amount of VP12 (ECL12) to the subject, wherein a cytotoxic agent, such as TAXOL, G-CSF, or a combination thereof, for example, can be administered to provide a combination therapy. And, in some embodiments, these methods can be accompanied by radiation therapy, surgical therapy, or a combination thereof.

In some embodiments, the methods can be directed to inhibiting or preventing angiogenesis, reversing angiogenesis, inhibiting or preventing tumor invasion, inhibiting or preventing the growth of solid tumors, reducing the size of solid tumors, or a combination thereof, in a subject. In these embodiments, as described above, the methods can further comprise the administration of an effective amount of an antiproliferative, an effective amount of radiation therapy, surgical therapy, or a combination thereof.

One of skill will appreciate that "tumor invasion" can be defined as the penetration of tissue barriers by migrating cancerous cells, and tumor invasion can be integral to metastases. Tumor invasion can include the invasion of surrounding tissue as the tumor grows, and capillary endothelial cells invade the tumor and create tumor blood vessels through, i.e., neovascularization of the tumor tissue. The tumor cells can also intravasate into the blood circulation for metastasis. Tumor cells can then arrest into distant organs, extravasate, and again migrate into the new site and start the invasive cycle again. As such, the inhibition or prevention of tumor invasion can contain a tumor or tumors and inhibit or prevent metastasis.

Uses and Methods of Administration

The compositions can provide a therapeutic and/or prophylactic effect in the treatment of a disease, or ameliorization of one or more symptoms of a disease in a subject. The term "subject" and "patient" are used interchangeably and refer to an animal such as a mammal including, but not limited to, non-primates such as, for example, a cow, pig, horse, cat, dog, rat and mouse; and primates such as, for example, a monkey or a human.

The compositions provided herein can be administered to a subject using any manner of administration known to one of skill. For example, in some embodiments, a localized administration is used and, in some embodiments a systemic administration is used. In some embodiments, a combination of system and local administration is used. One of skill will appreciate that the therapeutic program selected, the agents administered, the condition of the subject, and the effects desired, can affect the administration schedule and program used.

One of skill understands that the amount of the agents administered can vary according to factors such as, for example, the type of disease, age, sex, and weight of the subject, as well as the method of administration. For example, local and systemic administration can call for substantially different amounts to be effective. Dosage regimens may also be adjusted to optimize a therapeutic response. In some embodiments, a single bolus may be administered; several divided doses may be administered over time; the dose may be proportionally reduced or increased; or, any combination thereof, as indicated by the exigencies of the therapeutic situation and factors known one of skill in the art. It is to be noted that dosage values may vary with the severity of the condition to be alleviated. Dosage regimens may be adjusted over time according to the individual need and the professional judgment of the person administering or supervising the administration of the compositions, and the dosage ranges set forth herein are exemplary only and do not limit the dosage ranges that may be selected by medical practitioners.

The terms "administration" or "administering" refer to a method of incorporating a composition into the cells or tissues of a subject, either in vivo or ex vivo to diagnose, prevent, treat, or ameliorate a symptom of a disease. In one example, a compound can be administered to a subject in vivo parenterally. In another example, a compound can be administered to a subject by combining the compound with cell tissue from the subject ex vivo for purposes that include, but are not limited to, assays for determining utility and efficacy of a composition. When the compound is incorporated in the subject in combination with one or active agents, the terms "administration" or "administering" can include sequential or concurrent incorporation of the compound with the other agents such as, for example, any agent described above. A pharmaceutical composition of the invention is formulated to be compatible with its intended route of administration. Examples of routes of administration include, but are not limited to, parenteral such as, for example, intravenous, intradermal, intramuscular, and subcutaneous injection; oral; inhalation; intranasal; transdermal; transmucosal; and rectal administration.

An "effective amount" of a compound of the invention can be used to describe a therapeutically effective amount or a prophylactically effective amount. An effective amount can also be an amount that ameliorates the symptoms of a disease. A "therapeutically effective amount" refers to an amount that is effective at the dosages and periods of time necessary to achieve a desired therapeutic result and may also refer to an amount of active compound, prodrug or pharmaceutical agent that elicits any biological or medicinal response in a tissue, system, or subject that is sought by a researcher, veterinarian, medical doctor or other clinician that may be part of a treatment plan leading to a desired effect. In some embodiments, the therapeutically effective amount may need to be administered in an amount sufficient to result in amelioration of one or more symptoms of a disorder, prevention of the advancement of a disorder, or regression of a disorder. In some embodiments, for example, a therapeutically effective amount can refer to the amount of an agent that provides a measurable response of at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% of a desired action of the composition. The term "treating" refers to the administering one or more therapeutic or prophylactic agents taught herein.

A "prophylactically effective amount" refers to an amount that is effective at the dosages and periods of time necessary to achieve a desired prophylactic result such as, preventing, inhibiting, or reversing angiogenesis, tumor growth, or tumor invasion. Typically, a prophylactic dose is used in a subject prior to the onset of a disease, or at an early stage of the onset of a disease, to prevent or inhibit onset of the disease or symptoms of the disease. A prophylactically effective amount may be less than, greater than, or equal to a therapeutically effective amount.

The administration can be local or systemic. In some embodiments, the administration can be oral. In other embodiments, the administration can be subcutaneous injection. In other embodiments, the administration can be intravenous injection using a sterile isotonic aqueous buffer. In another embodiment, the administration can include a solubilizing agent and a local anesthetic such as lignocaine to ease discomfort at the site of injection. In other embodiments, the administrations may be parenteral to obtain, for example, ease and uniformity of administration.

The compounds can be administered in dosage units. The term "dosage unit" refers to discrete, predetermined quantities of a compound that can be administered as unitary dosages to a subject. A predetermined quantity of active compound can be selected to produce a desired therapeutic effect and can be administered with a pharmaceutically acceptable carrier. The predetermined quantity in each unit dosage can depend on factors that include, but are not limited to, (a) the unique characteristics of the active compound and the particular therapeutic effect to be achieved, and (b) the limitations inherent in the art of creating and administering such dosage units.

A "pharmaceutically acceptable carrier" is a diluent, adjuvant, excipient, or vehicle with which the composition is administered. A carrier is pharmaceutically acceptable after approval by a state or federal regulatory agency or listing in the U.S. Pharmacopeial Convention or other generally recognized sources for use in subjects.

The pharmaceutical carriers include any and all physiologically compatible solvents, dispersion media, coatings, antibacterial and antifungal agents, isotonic and absorption delaying agents, and the like. Examples of pharmaceutical carriers include, but are not limited to, sterile liquids, such as water, oils and lipids such as, for example, phospholipids and glycolipids. These sterile liquids include, but are not limited to, those derived from petroleum, animal, vegetable or synthetic origin such as, for example, peanut oil, soybean oil, mineral oil, sesame oil, and the like. Water can be a preferred carrier for intravenous administration. Saline solutions, aqueous dextrose and glycerol solutions can also be liquid carriers, particularly for injectable solutions.

Suitable pharmaceutical excipients include, but are not limited to, starch, sugars, inert polymers, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The composition can also contain minor amounts of wetting agents, emulsifying agents, pH buffering agents, or a combination thereof. The compositions can take the form of solutions, suspensions, emulsion, tablets, pills, capsules, powders, sustained-release formulations and the like. Oral formulations can include standard carriers such as, for example, pharmaceutical grades mannitol, lactose, starch, magnesium stearate, sodium saccharine, cellulose, magnesium carbonate, and the like. See Martin, E. W. Remington's Pharmaceutical Sciences. Supplementary active compounds can also be incorporated into the compositions.

In some embodiments, the carrier is suitable for parenteral administration. In other embodiments, the carrier can be suitable for intravenous, intraperitoneal, intramuscular, sublingual or oral administration. In other embodiments, the pharmaceutically acceptable carrier may comprise pharmaceutically acceptable salts.

Pharmaceutical formulations for parenteral administration may include liposomes. Liposomes and emulsions are delivery vehicles or carriers that are especially useful for hydrophobic drugs. Depending on biological stability of the therapeutic reagent, additional strategies for protein stabilization may be employed. Furthermore, one may administer the drug in a targeted drug delivery system such as, for example, in a liposome coated with target-specific antibody. The liposomes can be designed, for example, to bind to a target protein and be taken up selectively by the cell expressing the target protein.

Therapeutic compositions typically must be sterile and stable under the conditions of manufacture and storage. The composition can be formulated as a solution, microemulsion, liposome, or other ordered structure suitable for a high drug concentration. In some embodiments, the carrier can be a solvent or dispersion medium including, but not limited to, water; ethanol; a polyol such as for example, glycerol, propylene glycol, liquid polyethylene glycol, and the like; and, combinations thereof. The proper fluidity can be maintained in a variety of ways such as, for example, using a coating such as lecithin, maintaining a required particle size in dispersions, and using surfactants.

In some embodiments, isotonic agents can be used such as, for example, sugars; polyalcohols that include, but are not limited to, mannitol, sorbitol, glycerol, and combinations thereof; and sodium chloride. Sustained absorption characteristics can be introduced into the compositions by including agents that delay absorption such as, for example, monostearate salts, gelatin, and slow release polymers. Carriers can be used to protect active compounds against rapid release, and such carriers include, but are not limited to, controlled release formulations in implants and microencapsulated delivery systems. Biodegradable and biocompatible polymers can be used such as, for example, ethylene vinyl acetate, polyanhydrides, polyglycolic acid, collagen, polyorthoesters, polylactic acid, polycaprolactone, polyglycolic copolymer (PLG), and the like. Such formulations can generally be prepared using methods known to one of skill in the art.

The compounds may be administered as suspensions such as, for example, oily suspensions for injection. Lipophilic solvents or vehicles include, but are not limited to, fatty oils such as, for example, sesame oil; synthetic fatty acid esters, such as ethyl oleate or triglycerides; and liposomes. Suspensions that can be used for injection may also contain substances that increase the viscosity of the suspension such as, for example, sodium carboxymethyl cellulose, sorbitol, or dextran. Optionally, a suspension may contain stabilizers or agents that increase the solubility of the compounds and allow for preparation of highly concentrated solutions.

In one embodiment, a sterile and injectable solution can be prepared by incorporating an effective amount of an active compound in a solvent with any one or any combination of desired additional ingredients described above, filtering, and then sterilizing the solution. In another embodiment, dispersions can be prepared by incorporating an active compound into a sterile vehicle containing a dispersion medium and any one or any combination of desired additional ingredients described above. Sterile powders can be prepared for use in sterile and injectable solutions by vacuum drying, freeze-drying, or a combination thereof, to yield a powder that can be comprised of the active ingredient and any desired additional ingredients. Moreover, the additional ingredients can be from a separately prepared sterile and filtered solution. In another embodiment, the extract may be prepared in combination with one or more additional compounds that enhance the solubility of the extract.

In some embodiments, a therapeutically or prophylactically effective amount of a composition may range in concentration from about 0.001 nM to about 0.10 M; from about 0.001 nM to about 0.5 M; from about 0.01 nM to about 150 nM; from about 0.01 nM to about 500 μM; from about 0.01 nM to about 1000 nM, 0.001 μM to about 0.10 M; from about 0.001 μM to about 0.5 M; from about 0.01 μM to about 150 μM; from about 0.01 μM to about 500 μM; from about 0.01 μM to about 1000 nM, or any range therein. In some embodiments, the compositions may be administered in an amount ranging from about 0.001 mg/kg to about 500 mg/kg; from about 0.005 mg/kg to about 400 mg/kg; from about 0.01 mg/kg to about 300 mg/kg; from about 0.01 mg/kg to about 250 mg/kg; from about 0.1 mg/kg to about 200 mg/kg; from about 0.2 mg/kg to about 150 mg/kg; from about 0.4 mg/kg to about 120 mg/kg; from about 0.15 mg/kg to about 100 mg/kg, from about 0.15 mg/kg to about 50 mg/kg, from about 0.5 mg/kg to about 10 mg/kg, or any range therein, wherein a human subject is assumed to average about 70 kg.

In some embodiments, the compounds can be administered by inhalation through an aerosol spray or a nebulizer that may include a suitable propellant such as, for example, dichlorodifluoromethane, trichlorofluoromethane, dichlorotetrafluoroethane, carbon dioxide, or a combination thereof. In one example, a dosage unit for a pressurized aerosol may be delivered through a metering valve. In another embodiment, capsules and cartridges of gelatin, for example, may be used in an inhaler and can be formulated to contain a powderized mix of the compound with a suitable powder base such as, for example, starch or lactose.

The teachings herein encompass sustained release formulations for the administration of one or more agents. In some embodiments, the sustained release formulations can reduce the dosage and/or frequency of the administrations of such agents to a subject.

The compositions can be administered as a pharmaceutical formulation by injection. In some embodiments, the formulation can comprise the extract in combination with an aqueous injectable excipient. Examples of suitable aqueous injectable excipients are well known to persons of ordinary skill in the art, and they, and the methods of formulating the formulations, may be found in such standard references as Alfonso AR: Remington's Pharmaceutical Sciences, 17th ed., Mack Publishing Company, Easton Pa., 1985. Suitable aqueous injectable excipients include water, aqueous saline solution, aqueous dextrose solution, and the like, optionally containing dissolution enhancers for the acid-modified arabinogalactan protein composition, such as solution of mannitol or other sugars, or a solution of glycine or other amino acids.

Typically, a composition taught herein can be administered by subcutaneously, intramuscularly, intraperitoneally, or intravenously, injecting. A localized administration can, in some embodiments, include direct injection of an agent into the region of the tissue to be treated such as, for example, a solid tumor. In some embodiments, intravenous administration is used, and it can be continuous intravenous infusion over a period of a few minutes to an hour or more, such as around fifteen minutes. The amount administered may vary widely depending on the type of formulation, size of a unit dosage, kind of excipients, and other factors well known to those of ordinary skill in the art. The formulation may comprise, for example, from about 0.0001% to about 10% (w/w), from about 0.01% to about 1%, from about 0.1% to about 0.8%, or any range therein, with the remainder comprising the excipient or excipients.

In some embodiments, the composition can be administered in conjunction with at least one other therapeutic agent for the disease state being treated, especially another agent capable of treating cancer such as, for example, a chemotherapeutic agent. The amounts of the agents needed can be reduced, even substantially, such that the amount of the agent or agents required is reduced to the extent that a significant response is observed from the subject. A significant response can include, but is not limited to, a reduction or elimination of nausea, a visible increase in tolerance, a faster response to the treatment, a more selective response to the treatment, or a combination thereof.

The methods can further comprise the administration of an effective amount of an antiproliferative, an effective amount of radiation therapy, surgical therapy, or a combination thereof. The teachings are also directed to a method of treating a cancer. In some embodiments, the method comprises administering an agent to a subject in need of a cancer treatment, wherein the dose of the agent is selected to reduce or eliminate an immunosuppression that would otherwise occur when administering a substantially higher dose of the agent in the subject; and administering radiation therapy in combination with the agent, wherein the reduction or elimination of the immunosuppression enhances the efficacy of the radiation therapy when compared to the efficacy of the radiation therapy otherwise observed when administered in combination with the substantially higher dose of the agent in the subject. In some embodiments, the agent comprises one or more chemotherapeutic agents in combination with the agents provided herein. In these embodiments, the agent can be selected from the group consisting of dacarbazine, paclitaxel, doxorubicin, or a combination thereof.

In some embodiments, an effective amount can range, for example, from about 1 mg/day to about 1000 mg/day, from about 10 mg/day to about 500 mg/day, from about 50 mg/day to about 250 mg/day, or any range therein, for a human of average body mass. For treating a solid tumor, a similar amount will be therapeutically effective. A person of ordinary skill in the art will be able without undue experimentation, having regard to that skill and this disclosure, to determine a therapeutically effective amount of the compositions of this invention for a given disease.

In some embodiments, G-CSF is administered in combination with a composition taught herein using any amount, time, and method of administration known to be effective by one of skill. The G-CSF can be NEUPOGEN, for example, administered in an amount ranging from about 0.1 µg/kg to about 1 mg/kg, from about 0.5 µg/kg to about 500 µg/kg, from about 1 µg/kg to about 250 µg/kg, from about 1 µg/kg to about 100 µg/kg from about 1 µg/kg to about 50 µg/kg, or any range therein.

In some embodiments, the radiation therapy can be administered in a single, localized high-dose ranging, for example, from about 20 Gy to about 100 Gy. In some embodiments, the radiation therapy can be administered in a total dose ranging from about 20 Gy to about 100 Gy using a modified hypofractionation regime of dosing comprising from about 2 doses to about 5 doses during a time frame of one week. In some embodiments, the radiation therapy can be administered in a total dose ranging from about 20 Gy to about 100 Gy using a modified hypofractionation regime of dosing comprising from 2 doses to 3 doses during a time frame ranging from about 2 days to about 3 days. The radiation therapy can also be administered in a total dose ranging from about 45 Gy to about 60 Gy using a modified hypofractionation regime of dosing comprising administering a single dose ranging from about 15 Gy to about 20 Gy for each day during a 3-day time frame.

The compositions and therapies taught herein can be administered in combination. For example, the combinations can be administered, for example, for 30 minutes, 1 hour, 2 hours, 4 hours, 8 hours, 12 hours, 18 hours, 1 day, 2 days, 3 days, 4 days, 5 days, 6 days, 7 days, 8 days, 9 days, 10 days, 2 weeks, 3 weeks, 4 weeks, 6 weeks, 3 months, 6 months 1 year, any combination thereof, or any amount of time considered necessary by one of skill. The agents can be administered concomitantly, sequentially, or cyclically to a subject. Cycling therapy involves the administering a first agent for a predetermined period of time, administering a second agent or therapy for a second predetermined period of time, and repeating this cycling for any desired purpose such as, for example, to enhance the efficacy of the treatment. The agents can also be administered concurrently. The term "concurrently" is not limited to the administration of agents at exactly the same time, but rather means that the agents can be administered in a sequence and time interval such that the agents can work together to provide additional benefit. Each agent can be administered separately or together in any appropriate form using any appropriate means of administering the agent or agents.

Articles of Manufacture

The present invention provides for articles of manufacture that encompass finished, packaged and labelled pharmaceutical products. The articles of manufacture include the appropriate unit dosage form in an appropriate vessel or container such as, for example, a glass vial or other container that is hermetically sealed. In the case of dosage forms suitable for parenteral administration, the active ingredient, e.g. one or more agents including an extract taught herein, is sterile and suitable for administration as a particulate-free solution. In other words, the invention encompasses both parenteral solutions and lyophilized powders, each being sterile, and the latter being suitable for reconstitution prior to injection. Alternatively, the unit dosage form may be a solid suitable for oral, transdermal, topical or mucosal delivery.

In some embodiments, the unit dosage form is suitable for intravenous, intramuscular, topical or subcutaneous delivery. Thus, the invention encompasses solutions, which are preferably sterile and suitable for each route of delivery. The concentration of agents and amounts delivered are included as described herein.

As with any pharmaceutical product, the packaging material and container are designed to protect the stability of the product during storage and shipment. In addition, the articles of manufacture can include instructions for use or other information material that can advise the user such as, for example, a physician, technician or patient, regarding how to properly administer the composition as a prophylactic, therapeutic, or ameliorative treatment of the disease of concern. In some embodiments, instructions can indicate or suggest a dosing regimen that includes, but is not limited to, actual doses and monitoring procedures.

In other embodiments, the instructions can include informational material indicating that the administering of the compositions can result in adverse reactions including but not limited to allergic reactions such as, for example, anaphylaxis. The informational material can indicate that allergic reactions may exhibit only as mild pruritic rashes or may be severe and include erythroderma, vasculitis, anaphylaxis, Steven-Johnson syndrome, and the like. The informational material should indicate that anaphylaxis can be fatal and may occur when any foreign protein is introduced into the body. The informational material should indicate that these allergic reactions can manifest themselves as urticaria or a rash and develop into lethal systemic reactions and can occur soon after exposure such as, for example, within 10 minutes. The informational material can further indicate that an allergic reaction may cause a subject to experience paresthesia, hypotension, laryngeal edema, mental status changes, facial or pharyngeal angioedema, airway obstruction, bronchospasm, urticaria and pruritus, serum sickness, arthritis, allergic nephritis, glomerulonephritis, temporal arthritis, eosinophilia, or a combination thereof.

In some embodiments, the articles of manufacture can comprise one or more packaging materials such as, for example, a box, bottle, tube, vial, container, sprayer, insufflator, intravenous (I.V.) bag, envelope, and the like; and at least one unit dosage form of an agent comprising an extract taught herein within the packaging material. In other embodiments, the articles of manufacture may also include instructions for using the composition as a prophylactic, therapeutic, or ameliorative treatment for the disease of concern.

In other embodiments, the articles of manufacture can comprise one or more packaging materials such as, for example, a box, bottle, tube, vial, container, sprayer, insufflator, intravenous (I.V.) bag, envelope, and the like; and a first composition comprising at least one unit dosage form of an agent comprising an extract as taught herein within the packaging material, along with a second composition comprising a second agent such as, for example, a glycosaminoglycan, phospholipid, poly(alkylene glycol), any other bioactive agent taught herein, or any prodrugs, codrugs, metabolites, analogs, homologues, congeners, derivatives, salts and combinations thereof. In other embodiments, the articles of manufacture may also include instructions for using the composition as a diagnostic, prophylactic, therapeutic, or ameliorative treatment for the disease of concern.

Without intending to be limited to any theory or mechanism of action, the following examples are provided to further illustrate the teachings presented herein. It should be appreciated that there are several variations contemplated within the skill in the art, and that the examples are not intended to be construed as providing limitations to the claims.

Example 1

A Human Model was Prepared to Correlate Angiogenesis with the Extracellular Matrix In this study, we investigated the correlation between sprout angiogenesis and the integrity of an extracellular matrix (ECM) environment using in vivo and in vitro angiogenesis models. We used an $\alpha5\beta1$ antagonist and an $\alpha2\beta1$ antagonist in the models, where the $\alpha5\beta1$ antagonist was the disintegrin VLO4, and the $\alpha2\beta1$ antagonist was the disintegrin VP12 (ECL12).

Materials

A 3-D ECM model was prepared. Gelatin-coated, microcarrier beads (Cytodex-3) were purchased from Pharmacia (Uppsala, Sweden). Sterile, native bovine dermal collagen containing 95% type I collagen and 5% type III collagen (Vitrogen) was obtained from Collagen Biomaterials (Palo Alto, Calif.). Dimethyl dichlorosilane, aprotinin, dibutyryl cyclic AMP, hydrocortisone, trypsin, soybean trypsin inhibitor, and EDTA were obtained from Sigma Chemical Co. (St. Louis, Mo.). Endothelial cell basal medium (EBM), endothelial cell growth medium bulletkit-2 (EGM-2 BULLET-KIT), bovine brain extract, and epidermal growth factor were obtained from Clonetics Corp. (San Diego, Calif.). Normal human serum was obtained from BioWhittaker, Inc. (Walkersville, Md.). Platelet derived growth factor-BB (PDGF-BB), vascular endothelial cell growth factor (VEGF) and Basic fibroblast growth factor (bFGF) were purchased from Chemical Co. (St. Louis, Mo.). VEGF-C was kindly provided by Kari Alitalo. Human thrombin was obtained from Calbiochem (San Diego, Calif.). And, propidium iodide (PI) was obtained from Molecular Probes (Eugene, Oreg.).

Cell Culture

Human dermal microvascular endothelial cells (HDMEC) were isolated from human neonatal foreskins. Briefly, after initial harvest from minced trypsinized human foreskins, microvascular endothelial cells were further purified on a PERCOLL density gradient. HDMEC were cultured on collagen type 1 coated tissue culture flasks in EGM (endothelial cell growth medium) consisting of EBM supplemented with 10 ng/ml epidermal growth factor, 0.4% bovine brain extract, 17.5 µg/ml dibutyryl cyclic AMP, and 1 µg/ml hydrocortisone in the presence of 30% normal human serum. Endothelial cell cultures were characterized and determined to be >99% pure on the basis of formation of typical cobblestone monolayers in culture, positive immunostaining for factor VIII-related antigen, and selective uptake of acetylated low density lipoprotein. All experiments were done with HDMEC below passage 10. Bovine aortic endothelial cells (BAEC) were obtained from BioWhittaker, Inc. (Walkersville, Md.) and cultured according to manufacturer's instruction. BAEC between passage 4 and 8 were used for experiments.

Preparation of Endothelial Cell-Loaded Microcarrier Beads (EC-Beads)

Gelatin-coated CYTODEX-3 microcarrier beads were prepared as described by the manufacturer. Approximately 80,000 sterile microcarrier beads were washed, resuspended in EGM, and added to approximately 4.5 million endothelial cells (HDMEC or BAEC). The beads and cells were mixed by gentle swirling, incubated at 37° C. for 6 hr, and then rotated for 24-36 hrs on an orbital mixer in a 37° C. oven to generate endothelial cell-loaded microcarrier beads (EC-beads).

Example 2

Cell Migration and Capillary Sprout Formation was Identified in Fibrin Gels and Type I Collagen Gels in the Human Model FIGS. 1A-1C illustrate a study of human microvascular endothelial cell angiogenesis, according to some embodiments. A microcarrier, in vitro angiogenesis assay, previously designed to investigate bovine pulmonary artery endothelial cell angiogenic behavior in bovine fibrin gels, was modified for the study of human microvascular endothelial cell angiogenesis. The HDMEC were isolated from human neonatal foreskins and used, as described above, and images were captured at various magnifications, where the effect of angiogenic factors on sprout angiogenesis was quantified visually by counting the number and percent of EC-beads with capillary sprouts.

FIG. 1A shows the process in Step I, where human fibrinogen, isolated as previously described, was dissolved in M199 medium at a concentration of 1 mg/ml (pH 7.4) and sterilized by filtering through a 0.22 micron filter. An isotonic 1.5 mg/ml collagen solution was prepared by mixing sterile native bovine type I & III collagen (Vitrogen, Collagen Biomaterials, Palo Alto, Calif.) in 5XM199 medium and distilled water. The pH was adjusted to 7.4 using 1N NaOH.

FIG. 1A also shows the process in Step II, where in certain experiments, growth factors, such as VEGF, VEGF-C, bFGF or PDGF-BB, were added to the fibrinogen and collagen solutions.

For experiments using RGD peptides, EC-beads were firstly incubated with vary concentrations of peptides for one hour and then were added to the ECM solutions. About 500 EC-beads were then added to the ECM protein solutions, followed by the addition of 0.5 U/ml human thrombin. A 0.3 ml aliquot of each suspension was immediately added to appropriate wells of a 24-well tissue culture plate. After gelation, 1 ml of fresh assay medium (EBM supplemented with 20% normal human serum for HDMEC or EBM supplemented with 10% fetal bovine serum for BAEC) was added to each well.

FIGS. 1B and 1C show how the angiogenic response was monitored visually and recorded by video image capture. Specifically, capillary sprout formation was observed and recorded with a NIKON Diaphot-TMD inverted microscope (Nikon Inc., Melville, N.Y.), equipped with an incubator housing with a NIKON NP-2 thermostat and Sheldon #2004 carbon dioxide flow mixer. The microscope was directly interfaced to a video system consisting of a Dage-MTI CCD-72S video camera and Sony 12" PVM-122 video monitor linked to a Macintosh G3 computer. The images were captured at various magnifications using Adobe Photoshop. The effect of angiogenic factors on sprout angiogenesis was quantified visually by determining the number and percent of EC-beads with capillary sprouts. 100-200 beads (five random low power fields) in each of triplicate wells were counted for each experimental condition. All experiments were repeated at least three times. FIG. 1B shows an absence of sprout angiogenesis using anti-angiogenic factor, and FIG. 1C shows the presence of sprout angiogenesis using angiogenic factor.

Figure 2:
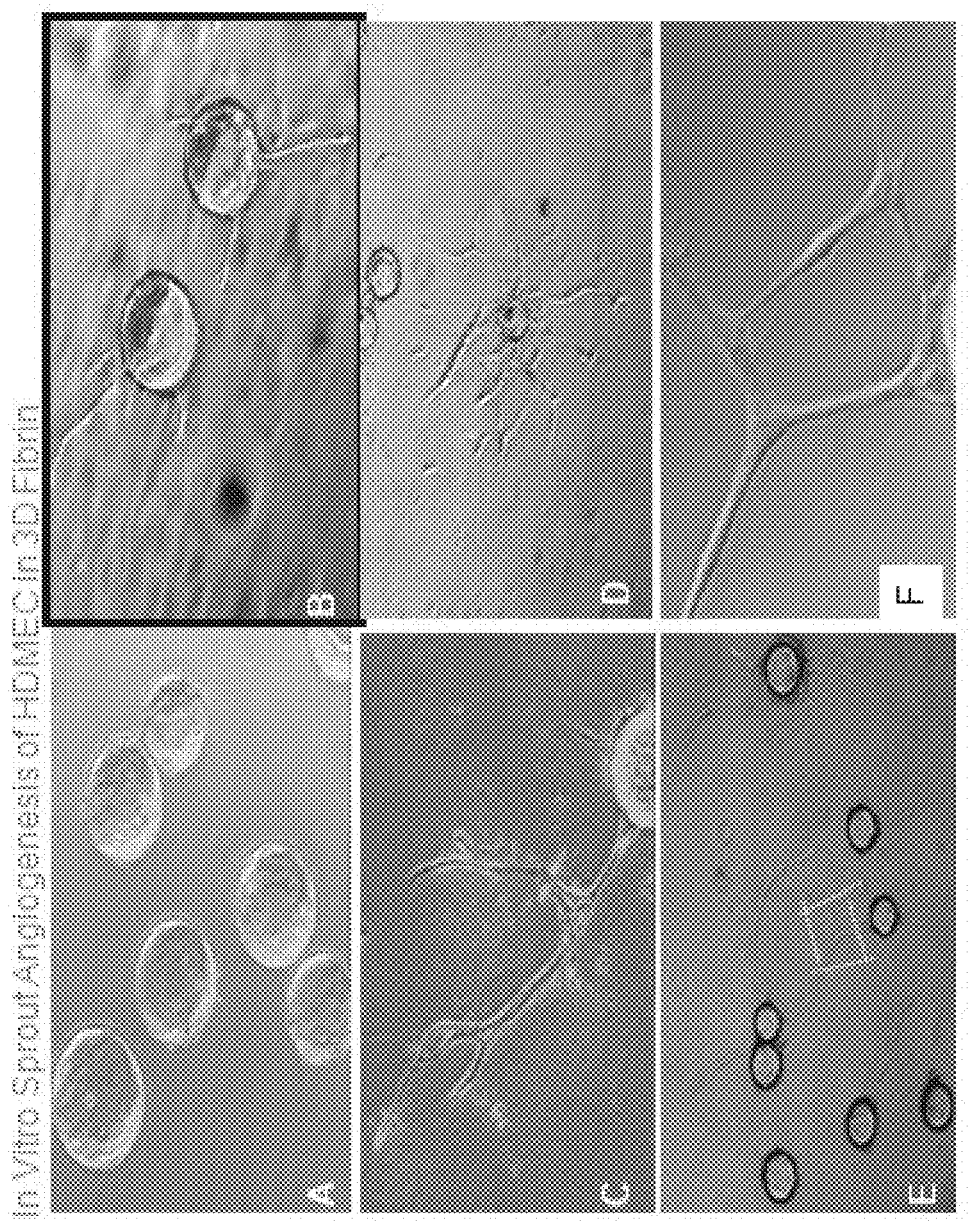
FIGS. 2A-2F show formation of angiogenic sprouts and capillary tube-like structures by HDMEC in fibrin stimulated by VEGF (100 ng/ml), according to some embodiments.
Figure 3:
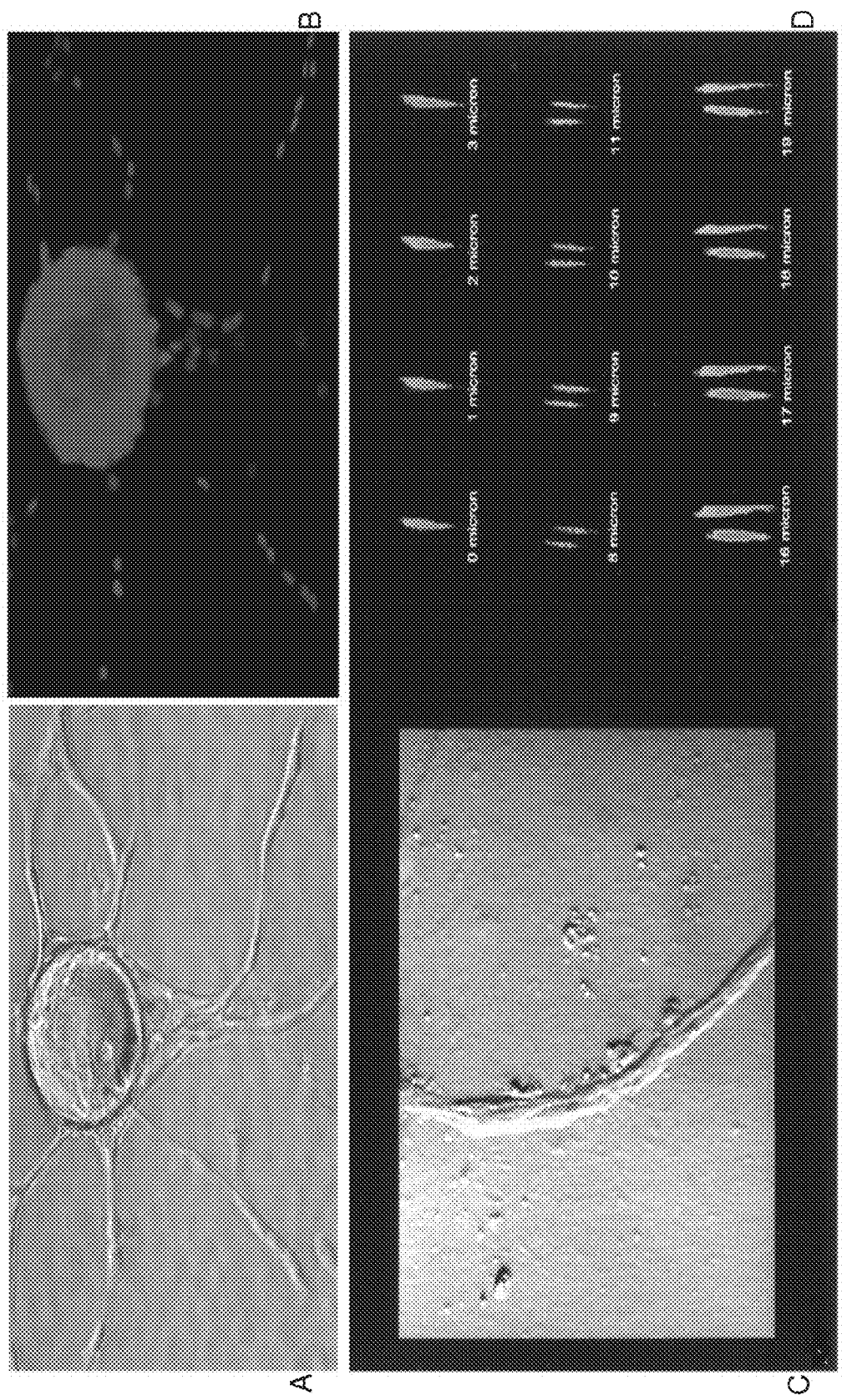
FIGS. 3A-3D show the presence of multiple cells in capillary tube-like structure by nuclei staining and presence of lumen demonstrated by confocal microscopic analysis, according to some embodiments.

FIGS. 2A-2F show formation of angiogenic sprouts and capillary tube-like structures by HDMEC in fibrin stimulated by VEGF (100 ng/ml), according to some embodiments. FIG. 2A illustrates what occurs in control fibrin gel without addition of angiogenic factors, where no significant sprout formation occurred after 48 hr. FIG. 2B illustrates that, in the presence of VEGF, HDMEC formed angiogenic sprouts and invaded and migrated into the fibrin gel within 48 hr. FIG. 2C shows that, by 5 days, VEGF-stimulated HDMEC formed branching capillary tube-like structures in the fibrin gel. FIG. 2D shows formation of local capillary arcades and networks by HDMEC in fibrin with VEGF for 5 days. FIG. 2E shows formation of wild capillary networks by HDMEC in fibrin with VEGF for 5 days. FIG. 2F, a higher magnification of a typical capillary network, illustrates that networks are formed as a result of branching and fusion of capillary tubes from neighboring beads. a) and b) 100×, c) and d) 400× magnification FIGS. 3A-3D show the presence of multiple cells in capillary tube-like structure by nuclei staining and presence of lumen demonstrated by confocal microscopic analysis, according to some embodiments. FIG. 3A shows HDMEC formed elongated and branched capillary sprouts in fibrin gel after 5 days in presence of VEGF at 100 ng/ml. In FIG. 3B, the culture in a) was fixed and stained with Propidium iodide (PI) to reveal nuclei. FIG. 3C shows a phase-contrast photomicrograph of typical capillary tube-like structure formed by HDMEC in fibrin with 100 ng/ml VEGF. FIG. 3D shows a series of contiguous 1 micron thick tangential cross sections of the capillary tube-like structure, obtained by reflective confocal microscopy with computerized imaging, initially revealed the top of the tube (0-3 microns) and then the presence of a central lumen (8-19 microns) between two walls. a) and b) 100×, c) and d) 400× magnification.

Figure 4:
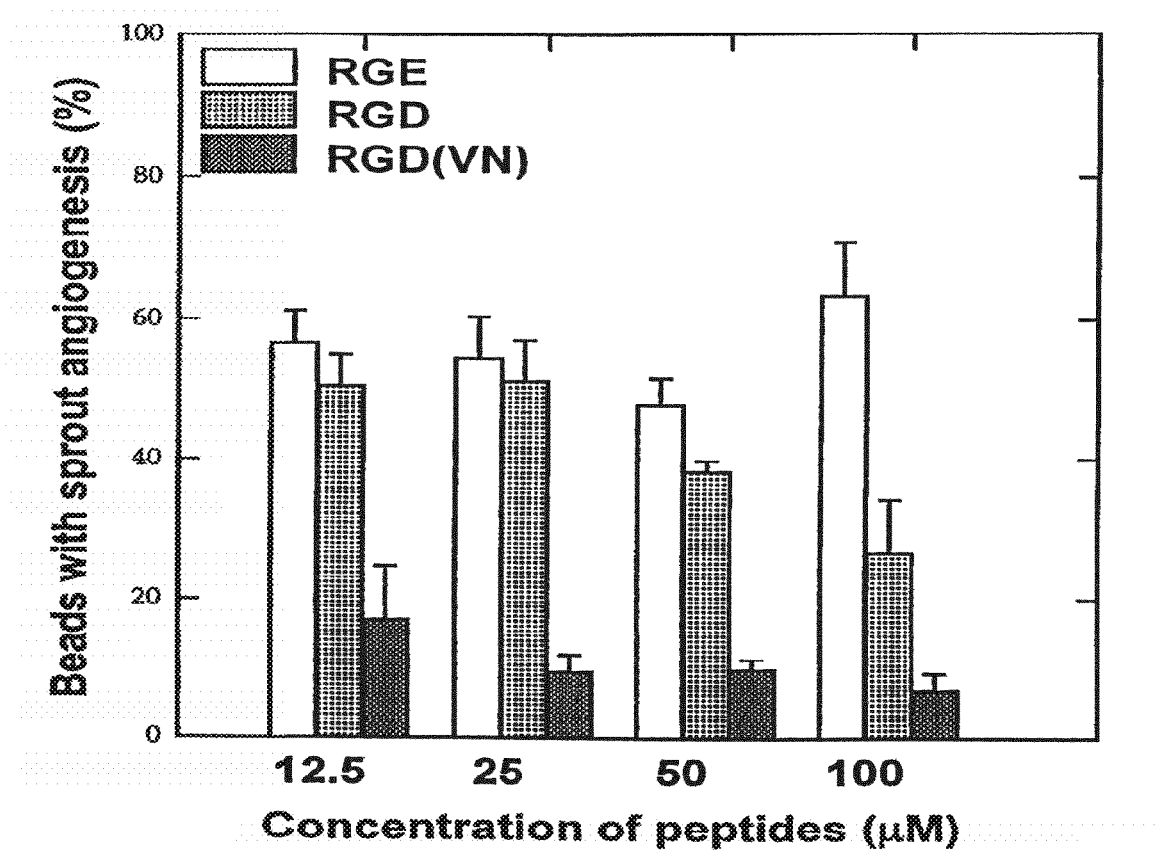
FIG. 4 graphically depicts the effect of GPenGRGDSPCA peptides [RGD(VN)] on sprout angiogenesis of HDMEC in fibrin, according to some embodiments.

FIG. 4 graphically depicts the effect of GPenGRGDSPCA peptides [RGD(VN)] on sprout angiogenesis of HDMEC in fibrin, according to some embodiments. GPenGRGDSPCA (SEQ ID NO:5) is a specific arginine-glycine-aspartic acid (RGD) antagonist HDMEC cultured on microcarrier beads were incubated with various doses of RGD[VN] (12.5 mM-100 mM) peptides at RT for 1 hr. The EC-beads were added to fibrinogen solution with presence of VEGF (100 ng/ml) and then polymerized with thrombin. RGD[VN] significantly inhibited sprout angiogenesis of HDMEC in fibrin compared to GRGESP[RGE] hexapeptide (SEQ ID NO:6) control peptides.

Figure 5:
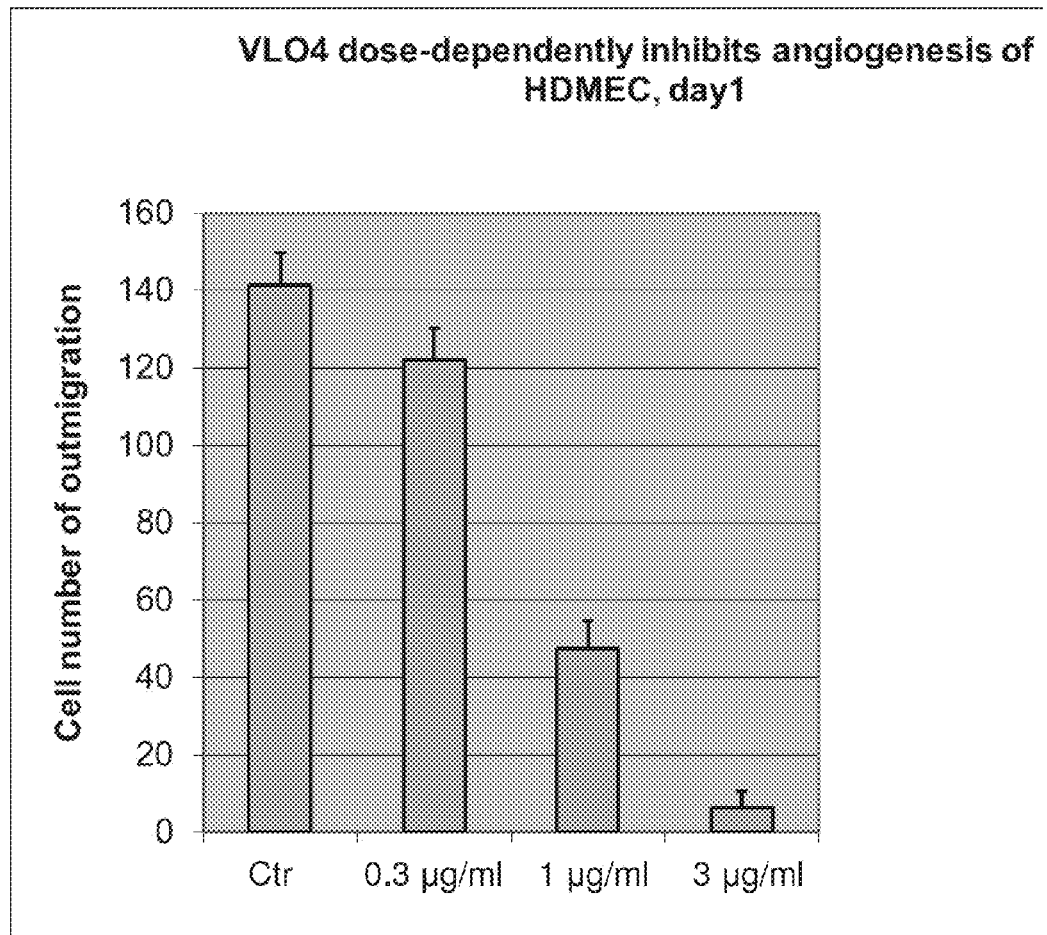
FIG. 5 graphically depicts the effect of VLO4 disintegrin on sprout angiogenesis of HDMEC in fibrin, according to some embodiments.
Figure 6:
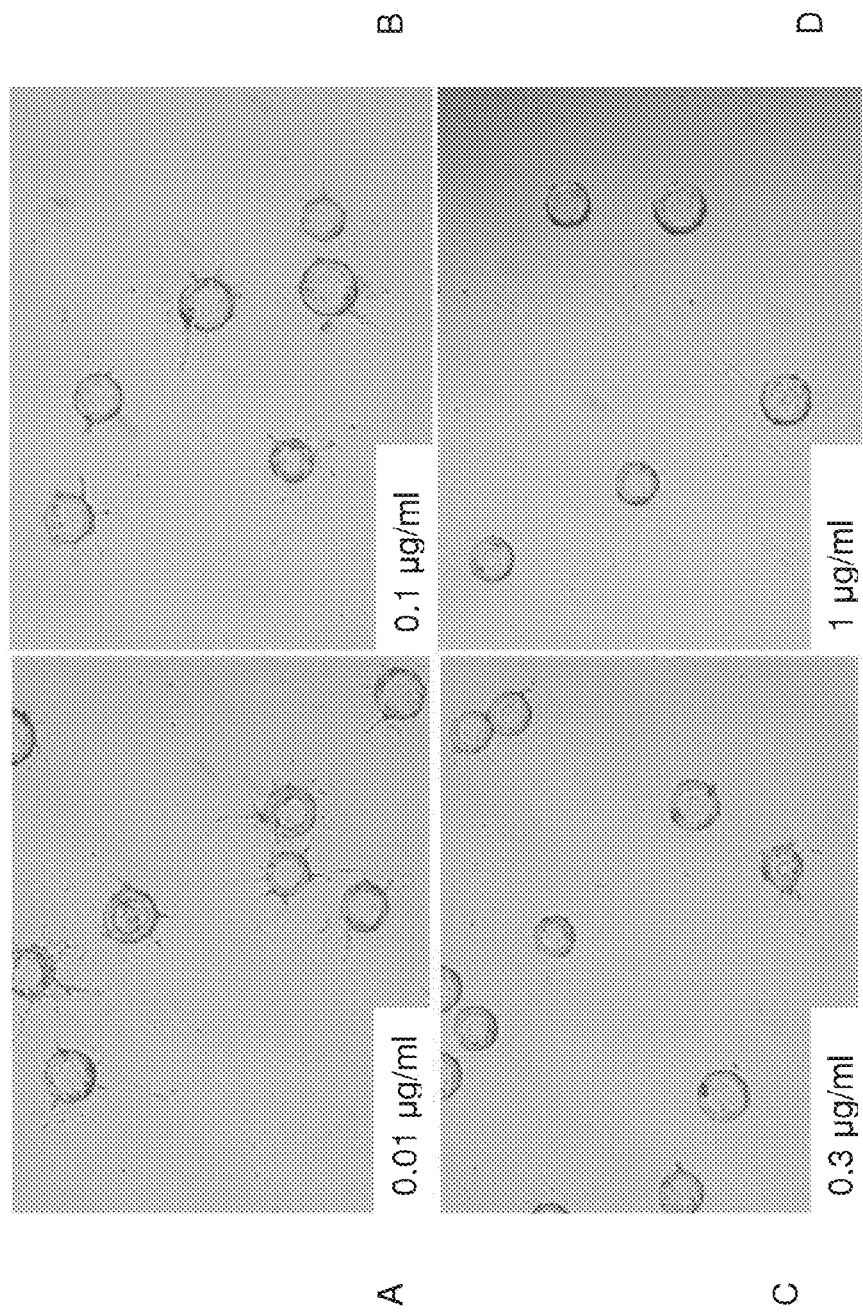
FIGS. 6A-6D show micrographs of the inhibitory effect of VLO4 disintergrin on sprout angiogenesis of HDMEC in fibrin, according to some embodiments.

FIG. 5 graphically depicts the effect of VLO4 disintegrin on sprout angiogenesis of HDMEC in fibrin, according to some embodiments. HDMEC cultured on microcarrier beads were incubated with various doses of VLO4 (0.3 µg/ml-3 µg/ml) at RT for 30 minutes. The EC-beads were added to fibrinogen solution with presence of VEGF (100 ng/ml) and then polymerized with thrombin. VLO4 dose-dependently inhibits sprout angiogenesis of HDMEC induced by VEGF in fibrin.

FIGS. 6A-6D show micrographs illustrating the effect of VLO4 disintegrin on sprout angiogenesis of HDMEC in fibrin, according to some embodiments. HDMEC cultured on microcarrier beads were incubated with various doses of VLO4 (0.01 µg/ml, 0.1 µg/ml, 0.3 µg/ml, and 1 µg/ml, FIGS. 6A-6D, respectively) at room temperature for 30 minutes. The EC-beads were added to fibrinogen solution with presence of VEGF (100 ng/ml) and then polymerized with thrombin. VLO4 dose-dependently inhibits sprout angiogenesis of HDMEC induced by VEGF in fibrin.

Figure 7:
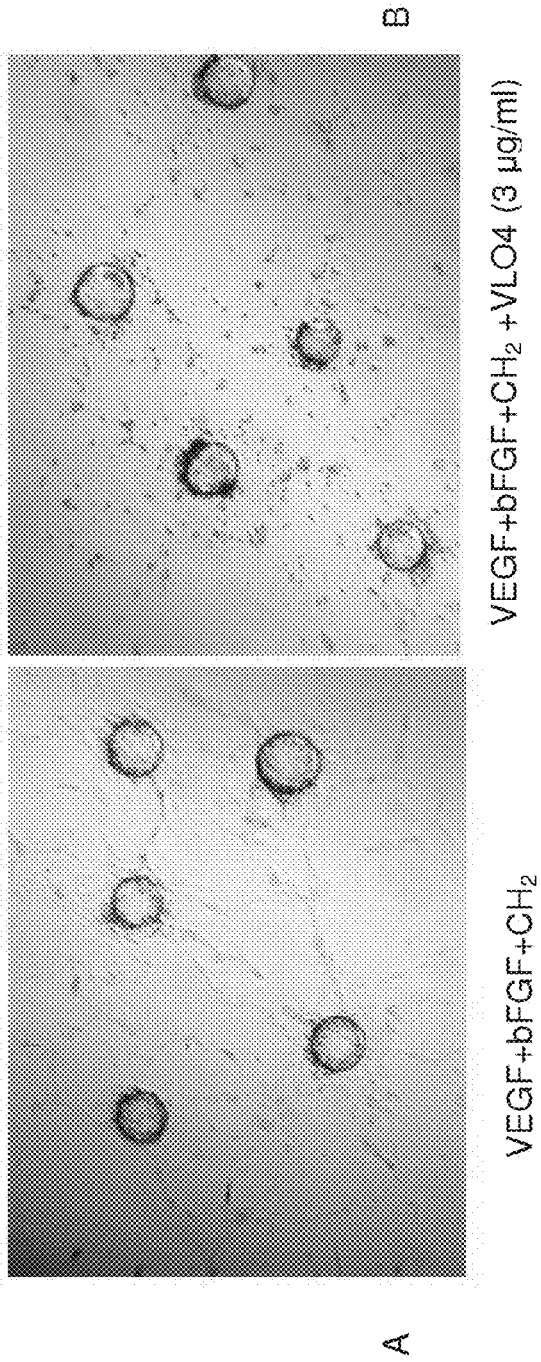
FIGS. 7A and 7B show micrographs of how VLO4 disintergrin disrupts newly formed angiogenic sprouts HDMEC in fibrin, according to some embodiments.

FIGS. 7A and 7B show micrographs of how VLO4 disintergrin disrupts newly formed angiogenic sprouts HDMEC in fibrin, according to some embodiments. HDMEC cultured on microcarriers beads were mixed with VEGF (30 ng/ml), bFGF (25 ng/ml) and heparin like polysaccharides $CH_2$ (10 µg/ml) various doses of VLO4 (0.01 µg/ml-1 µg/ml). The EC-beads were added to fibrinogen solution and then polymerized with thrombin. FIG. 7A shows that HDEMC formed extensive capillary sprouts in fibrin after 5 days. FIG. 7B shows that, where VLO4 (3 µg/ml) was added into the system on day 5, it totally disrupted the newly formed sprout angiogenesis within 24 hours.

Figure 8:
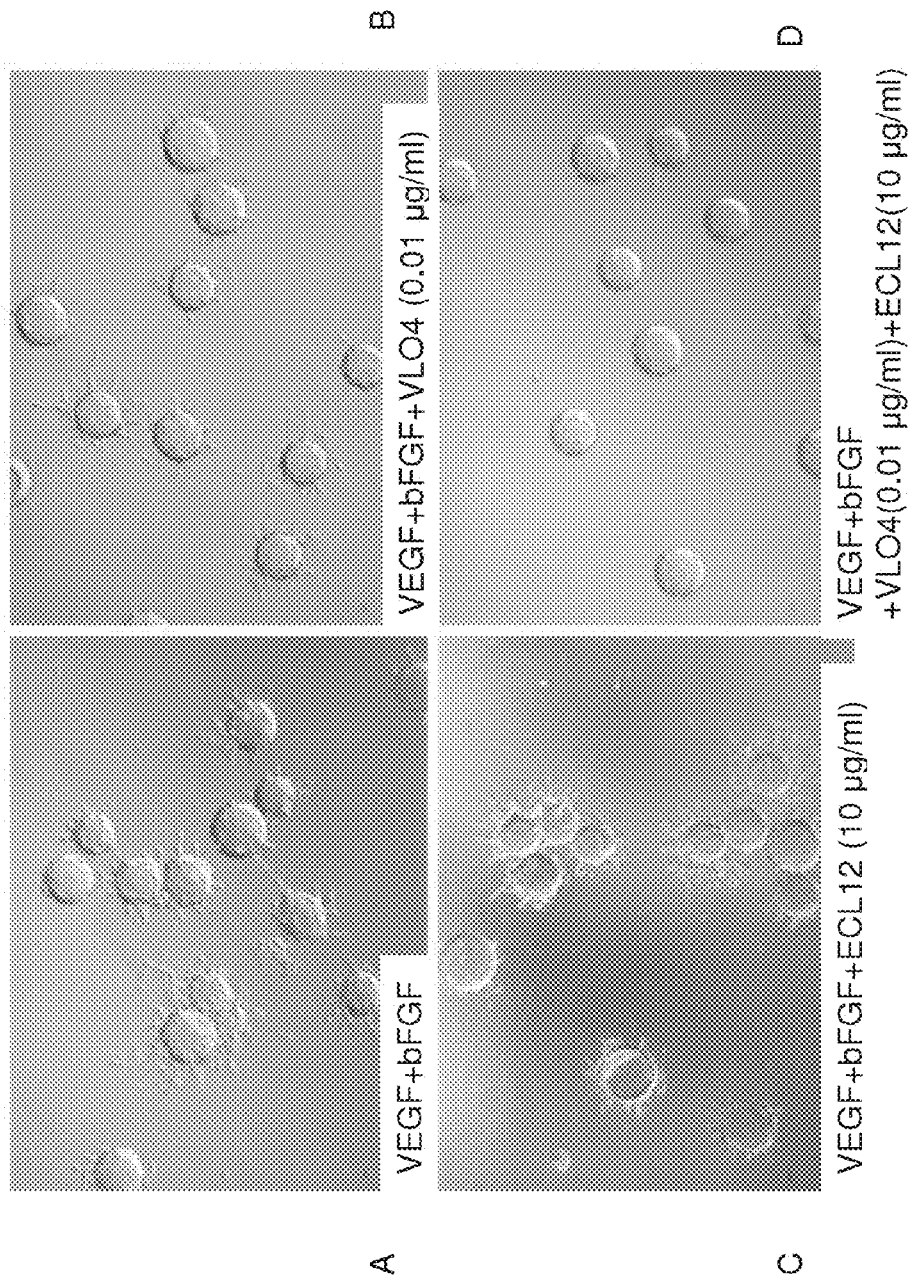
FIGS. 8A-8D are micrographs showing how VLO4 disintegrin (blocking integrin $\alpha5\beta1$) and VP12 disintegrin (ECL12, blocking integrin $\alpha2\beta1$) synergistically inhibited angiogenic sprouts of HDMEC in fibrin, according to some embodiments.

FIGS. 8A-8D are micrographs showing how VLO4 disintegrin (blocking integrin α5β1) and VP12 disintegrin (ECL12, blocking integrin α2β1) synergistically inhibited angiogenic sprouts of HDMEC in fibrin, according to some embodiments. HDMEC cultured on microcarriers beads were mixed with VEGF (30 ng/ml), bFGF (25 ng/ml) with or without VLO4 (0.01 µg/ml) and/or VP12 (10 µg/ml). The EC-beads were added to fibrinogen solution and then polymerized with thrombin. FIG. 8A shows that HDEMC formed extensive capillary sprouts of HDMEC induced by VEGF and bFGF in fibrin after 3 days. FIG. 8B shows that low doses of VLO4 (0.01 µg/ml) didn't significantly inhibit sprout angiogenesis of HDMEC. FIG. 8C shows that VP12 (10 µg/ml) didn't significantly inhibit sprout angiogenesis. FIG. 8D show that a combination of VLO4 and VP12 synergistically inhibited sprout angiogenesis in fibrin induced by VEGF and bFGF.

Figure 9:
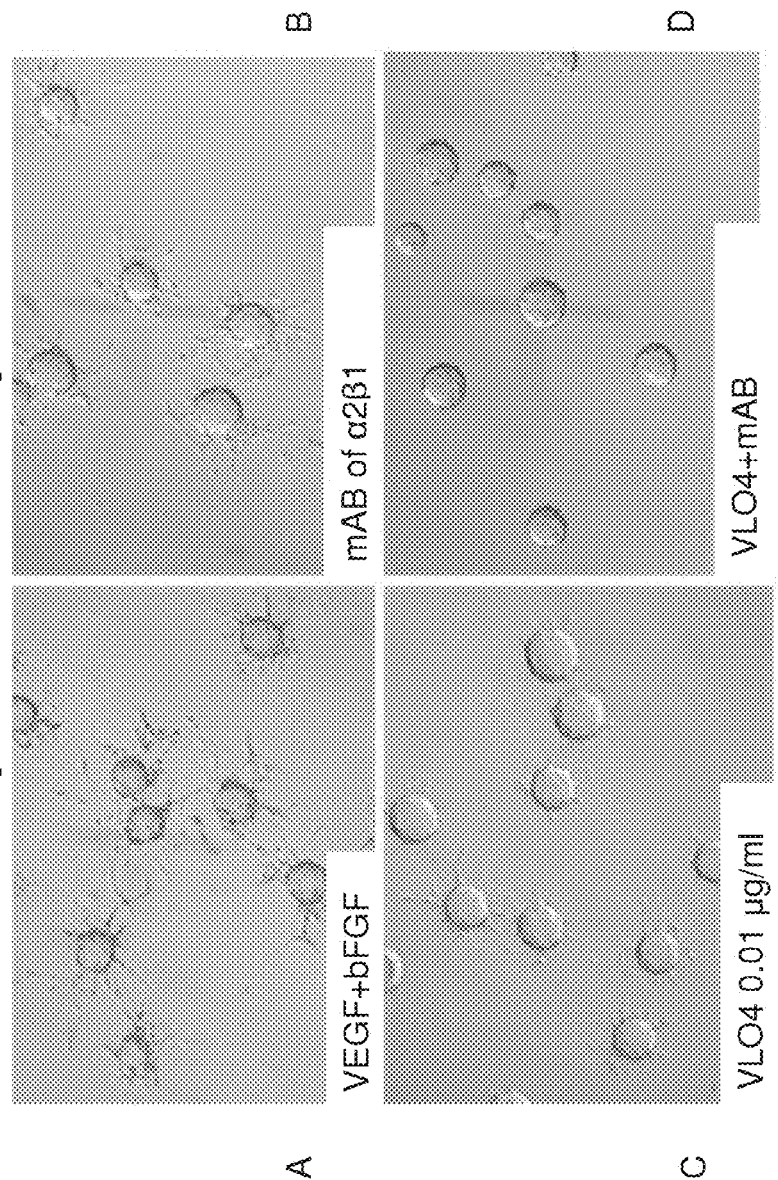
FIGS. 9A-9D are micrographs showing that VLO4 disintergrin (blocking intergrin $\alpha5\beta1$) and integrin $\alpha2\beta1$ blocking antibody synergistically inhibited angiogenic sprouts of HDMEC in fibrin, according to some embodiments.

FIGS. 9A-9D are micrographs showing that VLO4 disintergrin (blocking intergrin α5β1) and integrin α2β1 blocking antibody synergistically inhibited angiogenic sprouts of HDMEC in fibrin, according to some embodiments. HDMEC cultured on microcarrier beads were mixed with VEGF (30 ng/ml), bFGF (25 ng/ml) with or without VLO4 (0.01 µg/ml) and/or integrin α2β1 blocking antibody (5 µg/ml). The EC-beads were added to fibrinogen solution and then polymerized with thrombin. FIG. 9A shows that HDEMC formed extensive capillary sprouts of HDMEC induced by VEGF and bFGF in fibrin after 3 days. FIG. 9B shows that low doses of VLO4 (0.01 µg/ml) didn't significantly inhibit sprout angiogenesis of HDMEC. FIG. 9C shows that Integrin α2β1 blocking antibody didn't significantly inhibit sprout angiogenesis. FIG. 9D shows that a combination of VLO4 and integrin α2β1 blocking antibody synergistically inhibited sprout angiogenesis in fibrin induced by VEGF and bFGF.

Figure 10:
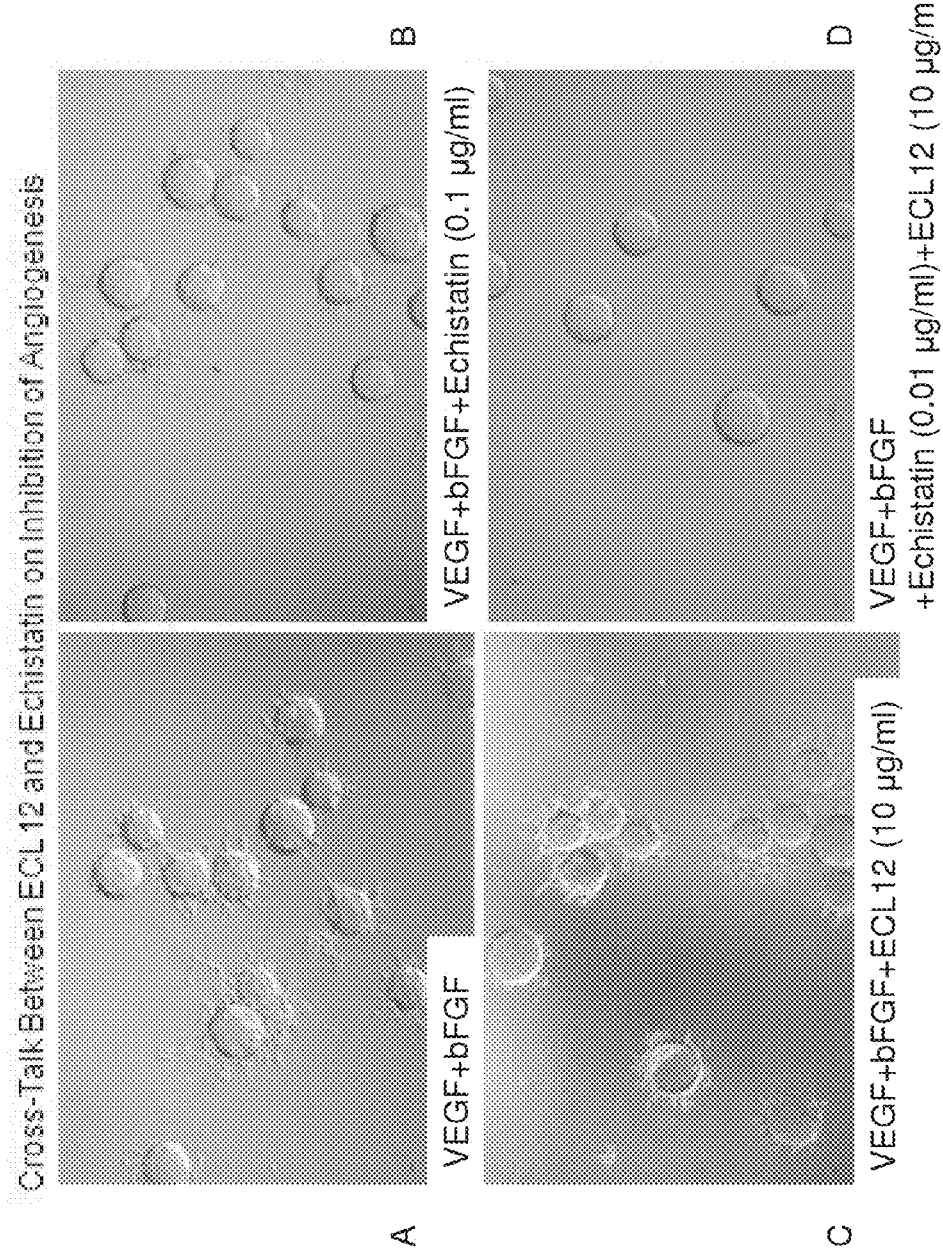
FIGS. 10A-10D are micrographs showing that Echistatin (blocking intergrin $\alpha v\beta3$) and VP12 disintegrin (ECL12, blocking integrin $\alpha2\beta1$) synergistically inhibited angiogenic sprouts of HDMEC in fibrin, according to some embodiments.

FIGS. 10A-10D are micrographs showing that Echistatin (blocking intergrin αvβ3) and VP12 disintegrin (ECL12, blocking integrin α2β1) synergistically inhibited angiogenic sprouts of HDMEC in fibrin, according to some embodiments. HDMEC cultured on microcarriers beads were mixed with VEGF (30 ng/ml), bFGF (25 ng/ml) with or without echistatin (0.1 µg/ml) and/or VP12 (10 µg/ml). The EC-beads were added to fibrinogen solution and then polymerized with thrombin. FIG. 10A shows that HDEMC formed extensive capillary sprouts of HDMEC induced by VEGF and bFGF in fibrin after 3 days. FIG. 10B shows that sow doses of echistatin (0.1 µg/ml) didn't significantly inhibit sprout angiogenesis of HDMEC. FIG. 10C shows that VP12 (10 µg/ml) didn't significantly inhibit sprout angiogenesis FIG. 10D shows that a combination of echistatin and VP12 synergistically inhibited sprout angiogenesis in fibrin induced by VEGF and bFGF.

Example 3

Analysis of an HT1080 Tumor Model

Figure 11:
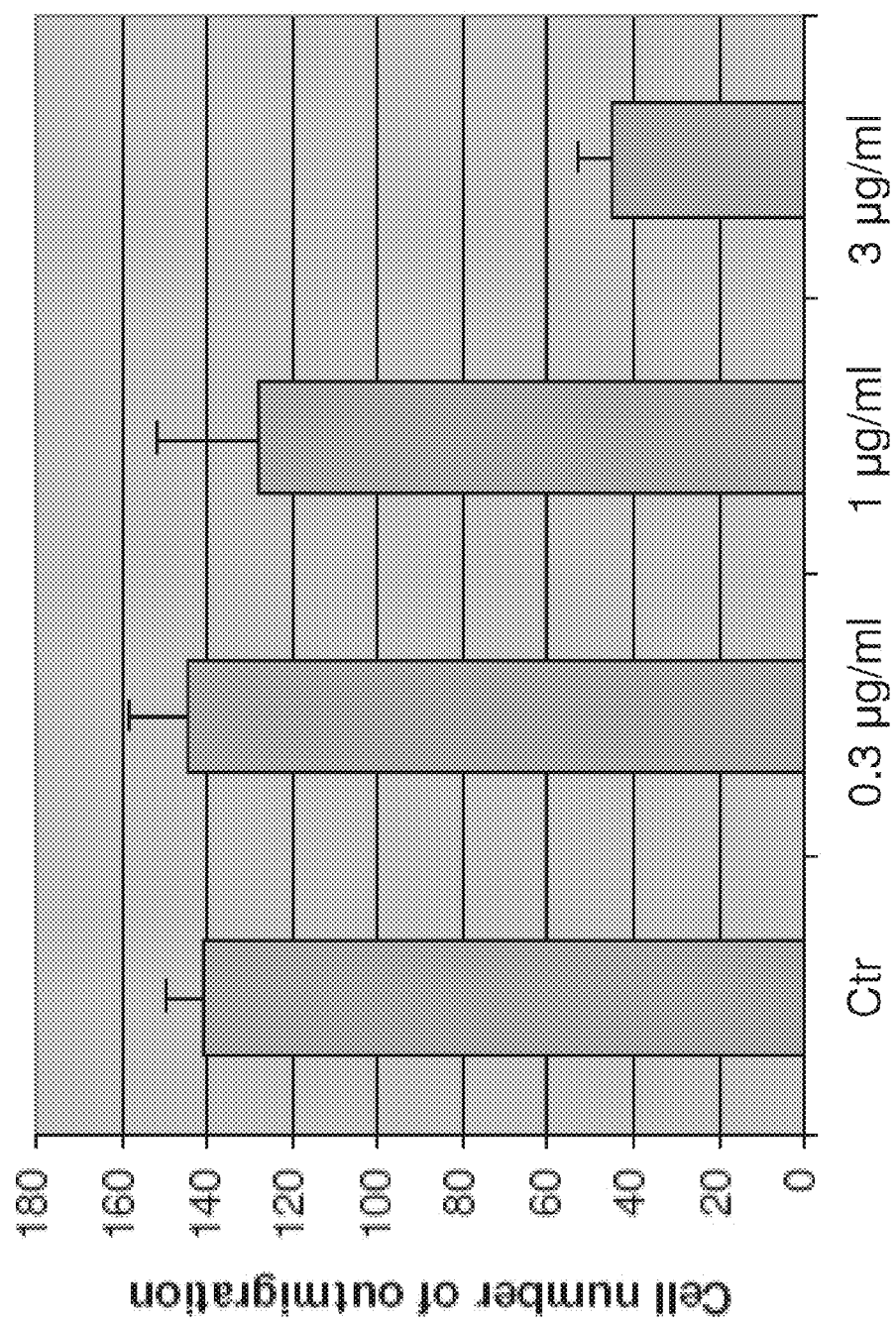
FIG. 11 graphically depicts how VLO4 (3 µg/ml) significantly inhibits HT1080 tumor cell invasion from contracted collagen into fibrin 3D matrices, according to some embodiments.

FIG. 11 graphically depicts how VLO4 (3 µg/ml) significantly inhibits HT1080 tumor cell invasion from contracted collagen into fibrin 3D matrices, according to some embodiments. Vlo4 dose dependently inhibits HT1080 tumor cells invade from contracted 3D collagen matrices into 3D fibrin matrices.

Figure 12:
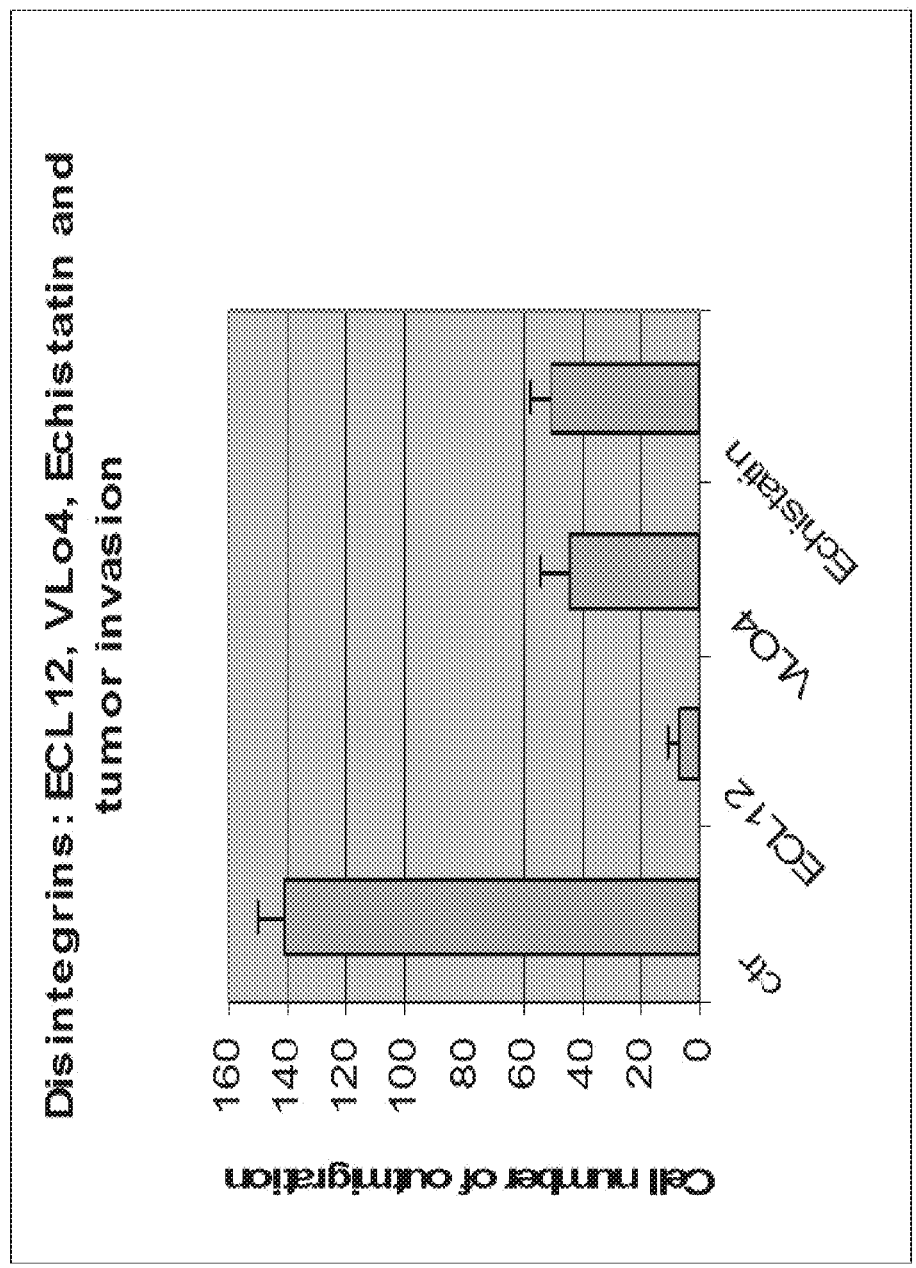
FIG. 12 graphically depicts how VP12 (3 µg/ml, EC12 blocking integrin $\alpha2\beta1$), VLO4 (3 µg/ml, blocking integrin $\alpha5\beta1$) and Echistatin (3 µg/ml) significantly inhibit HT1080 tumor cell invasion from contracted collagen into fibrin 3D matrices, according to some embodiments.

FIG. 12 graphically depicts how VP12 (3 µg/ml, EC12 blocking integrin α2β1), VLO4 (3 µg/ml, blocking integrin α5β1) and Echistatin (3 µg/ml) significantly inhibit HT1080 tumor cell invasion from contracted collagen into fibrin 3D matrices, according to some embodiments. It indicates that integrin αvβ3, integrin α2β1, and integrin α5β1 all play important role in tumor invasion.

Figure 13:
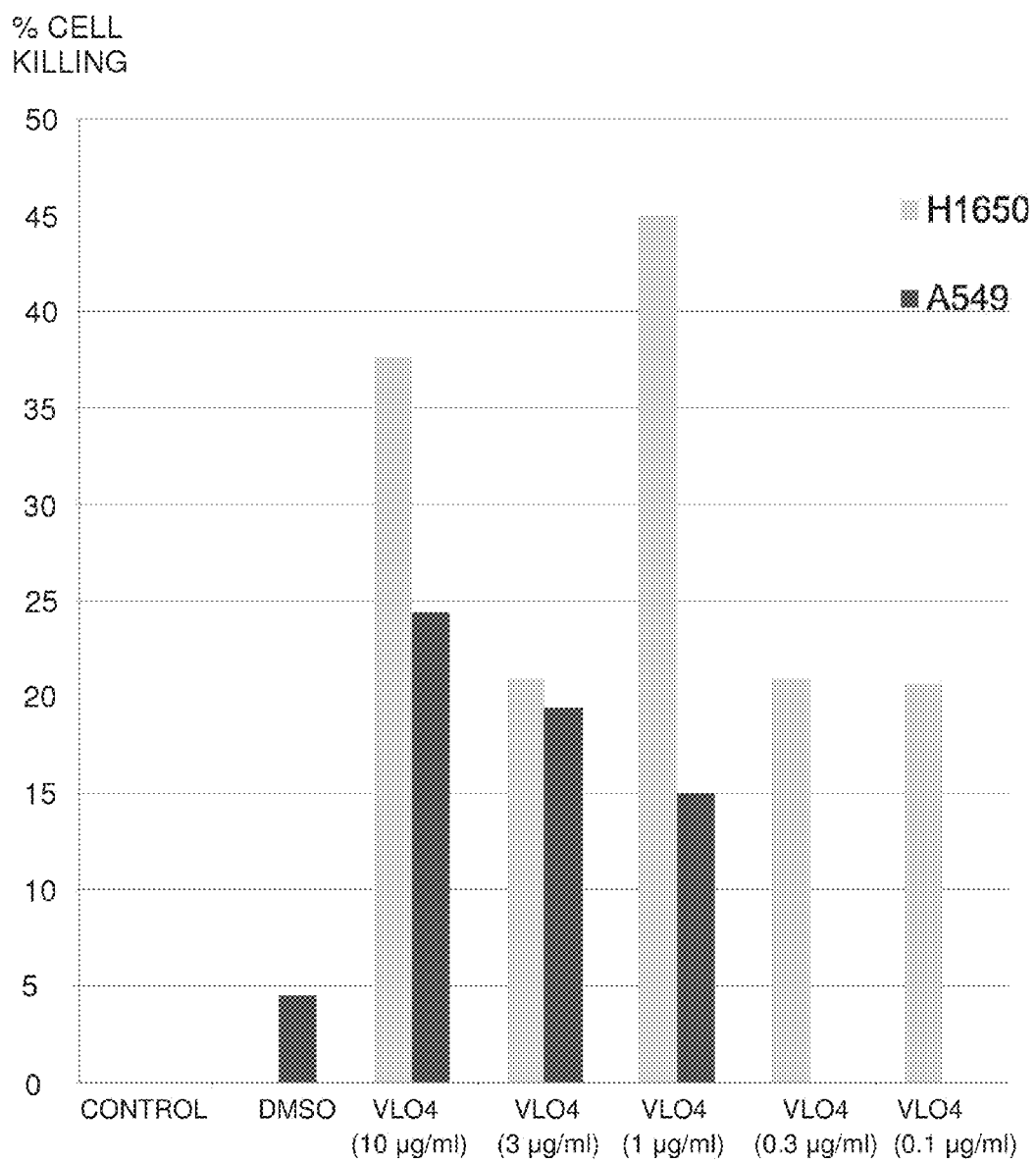
FIG. 13 graphically depicts how VLO4 significantly inhibited H1650 (Human metastatic lung cancer cell line) and A549 (human alveolar adenocarcinoma cell line) tumor cell proliferation, according to some embodiments.

FIG. 13 graphically depicts how VLO4 significantly inhibited H1650 (Human metastatic lung cancer cell line) and A549 (human alveolar adenocarcinoma cell line) tumor cell proliferation, according to some embodiments. It indicates that VLO4 not only inhibits tumor invasion, it also inhibits tumor cell proliferation.

Example 4

Fibrin and Collagen Receptors Synergistically Regulate Angiogenesis

We've shown that integrin (31 expression is highly up-regulated in fibrin rich, but not in collagen rich, matrix environments in vitro and in vivo. The 3D HDMEC model described above was used in this experiment that demonstrates combination therapy using two disintegrins, VLO4 and VP12 (ECL12).

Disintegrins represent a novel family of integrin β1 and β3 inhibitor proteins isolated from viper venoms. They are low molecular-weight, cysteine-rich peptides containing the Arg-Gly-Asp (RGD) sequence. They are the most potent known inhibitors of integrin function. Disintegrins interfere with cell adhesion to the extracellular matrix, including adhesion of melanoma cells and fibroblasts to fibronectin, and are potent inhibitors of platelet aggregation.

VLO4 is derived from the venom of *Vipera lebetina obtusa*. It is a potent irreversible α5β1 integrin antagonist. The following structure is a representation of VLO4, a 65 amino acid structure:

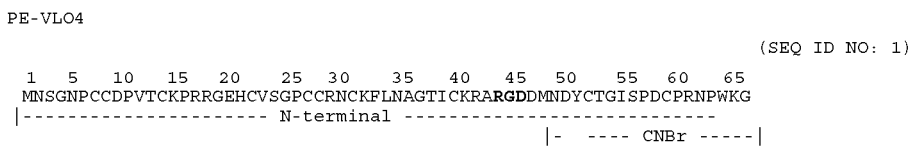

VLO4 can be requested, for example, from Sigma-aldrich. See CAS No. 105718. See also, Calvete, J. Biochem. J. 372: 725-734(2003), which is hereby incorporated by reference herein in its entirety.

VP12 (ECL12) (*Vipera paleastinae* venom or VP12) isolated from *Vipera paleastinae* venom showed a potent inhibitory activity against collagen receptors α2β1 integrins. Structurally, VP12 is composed of two subunits VP12A and VP12B displaying amino acid sequence homology with heterodimeric C-lectin type proteins. Sigma Aldrich offers *Vipera paleastinae* venom under catalog no. V0628, and the composition used for this example was graciously received from Dr. Cezary Marcinkiewicz, Biotechnology Center, Temple University College of Science and Technology, Philadelphia, Pa. 19122. See Cancer Biol Ther. 8(15):1507-16 (2009), which is hereby incorporated by reference herein in its entirety.

(SEQ ID NO: 2)

```
         1         10         20         30        40         49
VP12A  DQDCLPGWSFYEGNCYKAFDEPKSWVDAEKFCQKQSNGKHLASIEGLGK
VP12B  DQDCLPGWSYFEKYCYKVFQVKKNWEDAEKFCTEEVKDGHLISLH-SNE 50         60         70        80         90        100        109
 ANFVAKLVSEDQSETLREPQIHVWIGLRDQSERQQCSSH-WTDGSAVSYEXXXXXXXXXXXX
 EVEF--MTSL-AFPILKYD-I-VWMGLRNFW--RDCP-WKWSDDAKLDYKAWSDEP--NCYG 110        120        130
 XXXXXXXXXXXXXXXCGLAYPFICXXXX(...)   (SEQ ID NO: 2)
 AM-TTDY-QWLRWNCNDPRYFVCKSPA         (SEQ ID NO: 3)
```

The VP12 (ECL12) subunits VP12A and VP12B are shown, where the gray areas represent conserved amino acids, gaps (-) were included to maximize sequence similarities, and the X represents unidentified amino acids in the VP12A subunit. See also, Staniszewska, I. Cancer Biology & Therapy 8(15):1507-1516(2009), which is hereby incorporated by reference herein in its entirety.

FIGS. 7A-7D show synergistic inhibition of sprout angiogenesis when combining echistatin, an αvβ3 antagonist with VP12 (ECL12), an α2β1 agonist, according to some embodiments. FIG. 7A shows sprout angiogenesis in a HDMEC culture in VEGF and bFGF. FIG. 7B shows the inhibition of sprout angiogenesis when echistatin is added to the culture of FIG. 7A. FIG. 7C shows the inhibition of sprout angiogenesis when VP12 (ECL12) is added to the culture of FIG. 7A. FIG. 7D, however, shows the synergistic inhibition of sprout angiogenesis when both echistatin and VP12 (ECL12) are added to the culture of FIG. 7A.

Echistatin, a disintegrin specific for αvβ3, dose dependently inhibits sprout angiogenesis of HDMEC in fibrin. While VP12 (ECL12), a disintegrin inhibitor to collagen receptor integrin α2β1, has no inhibitory effect on sprout angiogenesis in vitro. Surprisingly, however, this example illustrates how VP12 (ECL12) significantly and synergistically enhanced the inhibition of sprout angiogenesis by echistatin when administered in combination with echistatin Echistatin (Disintegrin echistatin-alpha or Carinatin) is derived from the venom of *Echis carinatus* (Saw-scaled viper). It is a potent irreversible αvβ3 integrin antagonist that disrupts attachment of osteoclasts to bone and inhibits bone reabsorption, prevents ADP-induced platelet aggregation via inhibition of glycoprotein IIb/IIIa (GpIIb/IIIa, αIIβ3) receptors. Echistatin inhibits fibrinogen interaction with platelet receptors expressed on the glycoprotein IIb-IIIa complex, acts by binding to the glycoprotein IIb-IIIa receptor on the platelet surface, and inhibits aggregation induced by ADP, thrombin, platelet-activating factor and collagen. The following structure is a representation of echastatin, a 49 amino acid structure for echistatin:

```
                                              (SEQ ID NO: 4)
    1         10         20         30          40
 QCESGPCCRN CKFLKEGTIC KRARGDDMDD YCNGKTCDCP

49
 RNPHKGPAT
```

Echistatin is commercially available, for example, from Sigma-aldrich. See CAS Nos. 129038-42-2 and 154303-05-6. See also, Calvete, J. Biochem. J. 372:725-734(2003), which is hereby incorporated by reference herein in its entirety.

I claim:

1. A method of inhibiting angiogenesis in a subject in need thereof, comprising administering in combination to the subject (i) an amount of VLO4 ranging from 0.01 µg/ml-10 µg/ml in combination with (ii) an amount of VP12 (ECL12) ranging from 0.01 µg/ml-10 µg/ml to the subject that would be less than a therapeutically effective amount of the VP12 (ECL12) administered alone; and, inhibiting angiogenesis in the subject.

2. The method of claim 1, wherein the method further inhibits lung tumor invasion.

3. The method of claim 1, wherein the method further inhibits the growth of solid lung tumors.

4. The method of claim 1, further comprising the administration of an effective amount of an antiproliferative.

5. The method of claim 1, further comprising the administration of an effective amount of radiation therapy.

6. The method of claim 1, further comprising the administration of an effective amount of chemotherapy.

7. A method of inhibiting the growth of a solid lung tumor in a subject in need thereof, comprising administering in combination to the subject (i) an amount of VLO4 ranging from 0.01 µg/ml-10 µg/ml that would be less than a therapeutically effective amount of the VLO4 administered alone, and (ii) an amount of VP12 (ECL12) ranging from 0.01 µg/ml-10 µg/ml that would be less than a therapeutically effective amount of the VP12 (ECL12) administered alone; and, inhibiting growth of the solid lung tumor in the subject.

8. The method of claim 7, wherein the method further inhibits lung tumor invasion.

9. The method of claim 7, further comprising the administration of an effective amount of an antiproliferative.

10. The method of claim 7, further comprising the administration of an effective amount of radiation therapy.

11. The method of claim 7, further comprising the administration of an effective amount of chemotherapy.

12. A method of inhibiting lung tumor invasion in a subject in need thereof, comprising administering in combination to the subject (i) an amount of VLO4 ranging from 0.01 µg/ml-10 µg/ml that would be less than a therapeutically effective amount of the VLO4 administered alone, and (ii) an amount of VP12 (ECL12) ranging from 0.01 µg/ml-10 µg/ml that would be less than a therapeutically effective amount of the VP12 (ECL12) administered alone; and, inhibiting lung tumor invasion in the subject.

13. The method of claim 12, wherein the method inhibits the growth of solid lung tumors.

14. The method of claim 12, further comprising the administration of an effective amount of an antiproliferative.

15. The method of claim 12, further comprising the administration of an effective amount of radiation therapy.

16. The method of claim 12, further comprising the administration of an effective amount of chemotherapy.

17. A method of disrupting angiogenesis in a subject in need thereof, comprising administering an effective amount of VLO4 to the subject.

18. The method of claim 17, comprising administering VLO4 and VP12 (ECL12) to the subject.

19. The method of claim 17, wherein the method further inhibits lung tumor invasion.

20. The method of claim 17, wherein the method inhibits the growth of solid lung tumors.

21. The method of claim 17, further comprising the administration of an effective amount of an antiproliferative.

22. The method of claim 17, further comprising the administration of an effective amount of radiation therapy.

23. The method of claim 17, further comprising the administration of an effective amount of chemotherapy.

24. A method of disrupting angiogenesis in a subject in need thereof, comprising administering in combination to the subject (i) an effective amount of VLO4 ranging from 0.01 μg/ml-10 μg/ml that would be less than a therapeutically effective amount of the VLO4 administered alone, and (ii) an amount of VP12 (ECL12) ranging from 0.01 μg/ml-10 μg/ml; and, disrupting angiogenesis in the subject.

25. The method of claim 24, wherein the method further inhibits tumor invasion.

26. The method of claim 24, wherein the method further inhibits the growth of solid lung tumors.

27. The method of claim 24, further comprising the administration of an effective amount of an antiproliferative.

28. The method of claim 24, further comprising the administration of an effective amount of radiation therapy.

29. The method of claim 24, further comprising the administration of an effective amount of chemotherapy.

* * * * *

SEQUENCE LISTING

```
<160> NUMBER OF SEQ ID NOS: 6

<210> SEQ ID NO 1
<211> LENGTH: 65
<212> TYPE: PRT
<213> ORGANISM: Vipera lebetina

<400> SEQUENCE: 1

Met Asn Ser Gly Asn Pro Cys Cys Asp Pro Val Thr Cys Lys Pro Arg
1               5                   10                  15

Arg Gly Glu His Cys Val Ser Gly Pro Cys Cys Arg Asn Cys Lys Phe
            20                  25                  30

Leu Asn Ala Gly Thr Ile Cys Lys Arg Ala Arg Gly Asp Asp Met Asn
        35                  40                  45

Asp Tyr Cys Thr Gly Ile Ser Pro Asp Cys Pro Arg Asn Pro Trp Lys
    50                  55                  60

Gly
65

<210> SEQ ID NO 2
<211> LENGTH: 137
```

```
<212> TYPE: PRT
<213> ORGANISM: Vipera palestinae
<220> FEATURE:
<221> NAME/KEY: MOD_RES
<222> LOCATION: (99)..(124)
<223> OTHER INFORMATION: Any amino acid
<220> FEATURE:
<221> NAME/KEY: MOD_RES
<222> LOCATION: (134)..(137)
<223> OTHER INFORMATION: Any amino acid

<400> SEQUENCE: 2

Asp Gln Asp Cys Leu Pro Gly Trp Ser Phe Tyr Glu Gly Asn Cys Tyr
1               5                   10                  15

Lys Ala Phe Asp Glu Pro Lys Ser Trp Val Asp Ala Glu Lys Phe Cys
            20                  25                  30

Gln Lys Gln Ser Asn Gly Lys His Leu Ala Ser Ile Glu Gly Leu Gly
        35                  40                  45

Lys Ala Asn Phe Val Ala Lys Leu Val Ser Glu Asp Gln Ser Glu Thr
    50                  55                  60

Leu Arg Glu Pro Gln Ile His Val Trp Ile Gly Leu Arg Asp Gln Ser
65                  70                  75                  80

Glu Arg Gln Gln Cys Ser Ser His Trp Thr Asp Gly Ser Ala Val Ser
                85                  90                  95

Tyr Glu Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Cys Gly Leu Ala
        115                 120                 125

Tyr Pro Phe Ile Cys Xaa Xaa Xaa Xaa
    130                 135

<210> SEQ ID NO 3
<211> LENGTH: 125
<212> TYPE: PRT
<213> ORGANISM: Vipera palestinae

<400> SEQUENCE: 3

Asp Gln Asp Cys Leu Pro Gly Trp Ser Tyr Phe Glu Lys Tyr Cys Tyr
1               5                   10                  15

Lys Val Phe Gln Val Lys Lys Asn Trp Glu Asp Ala Glu Lys Phe Cys
            20                  25                  30

Thr Glu Glu Val Lys Asp Gly His Leu Ile Ser Leu His Ser Asn Glu
        35                  40                  45

Glu Val Glu Phe Met Thr Ser Leu Ala Phe Pro Ile Leu Lys Tyr Asp
    50                  55                  60

Ile Val Trp Met Gly Leu Arg Asn Phe Trp Arg Asp Cys Pro Trp Lys
65                  70                  75                  80

Trp Ser Asp Asp Ala Lys Leu Asp Tyr Lys Ala Trp Ser Asp Glu Pro
                85                  90                  95

Asn Cys Tyr Gly Ala Met Thr Thr Asp Tyr Gln Trp Leu Arg Trp Asn
            100                 105                 110

Cys Asn Asp Pro Arg Tyr Phe Val Cys Lys Ser Pro Ala
        115                 120                 125

<210> SEQ ID NO 4
<211> LENGTH: 49
<212> TYPE: PRT
<213> ORGANISM: Echis carinatus

<400> SEQUENCE: 4
```

```
Gln Cys Glu Ser Gly Pro Cys Cys Arg Asn Cys Lys Phe Leu Lys Glu
1               5                   10                  15

Gly Thr Ile Cys Lys Arg Ala Arg Gly Asp Asp Met Asp Asp Tyr Cys
            20                  25                  30

Asn Gly Lys Thr Cys Asp Cys Pro Arg Asn Pro His Lys Gly Pro Ala
        35                  40              45

Thr

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Pen

<400> SEQUENCE: 5

Gly Xaa Gly Arg Gly Asp Ser Pro Cys Ala
1               5                   10

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Arg Gly Glu Ser Pro
1               5
```